(12) United States Patent
Colson et al.

(10) Patent No.: US 7,687,521 B2
(45) Date of Patent: *Mar. 30, 2010

(54) DIALKYLPHENYL COMPOUNDS HAVING BETA2 ADRENERGIC RECEPTOR AGONIST AND MUSCARINIC RECEPTOR ANTAGONIST ACTIVITY

(75) Inventors: Pierre-Jean Colson, San Francisco, CA (US); Adam D. Hughes, Belmont, CA (US); Craig Husfeld, Redwood City, CA (US); Mathai Mammen, Menlo Park, CA (US); Miroslav Rapta, Sunnyvale, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/406,283

(22) Filed: Mar. 18, 2009

(65) Prior Publication Data

US 2009/0176833 A1 Jul. 9, 2009

Related U.S. Application Data

(62) Division of application No. 11/789,300, filed on Apr. 24, 2007, now Pat. No. 7,524,965.

(60) Provisional application No. 60/794,702, filed on Apr. 25, 2006.

(51) Int. Cl.
A61K 31/445 (2006.01)
(52) U.S. Cl. .................................................. 514/317
(58) Field of Classification Search .................. 514/317
See application file for complete search history.

(56) References Cited

U.S. PATENT DOCUMENTS

| | | | |
|---|---|---|---|
| 6,268,533 B1 | 7/2001 | Gao et al. | |
| 6,576,793 B1 | 6/2003 | Moran et al. | |
| 6,670,376 B1 | 12/2003 | Moran et al. | |
| 6,693,202 B1 | 2/2004 | Aggen et al. | |
| 7,141,671 B2 | 11/2006 | Mammen et al. | |
| 7,345,175 B2 | 3/2008 | Mammen et al. | |
| 7,355,046 B2 | 4/2008 | Mammen et al. | |
| 7,507,751 B2 | 3/2009 | Mammen et al. | |
| 7,514,558 B2 | 4/2009 | Mammen et al. | |
| 7,521,561 B2 | 4/2009 | Mammen et al. | |
| 7,524,959 B2 | 4/2009 | Mammen et al. | |
| 7,524,965 B2 | 4/2009 | Colson et al. | |
| 7,528,253 B2 | 5/2009 | Mammen et al. | |
| 2003/0018019 A1 | 1/2003 | Meade et al. | |
| 2004/0209860 A1 | 10/2004 | Mammen et al. | |
| 2004/0209915 A1 | 10/2004 | Mammen et al. | |
| 2006/0035933 A1 | 2/2006 | Mammen et al. | |
| 2006/0223860 A1 | 10/2006 | Mammen et al. | |
| 2007/0208176 A1 | 9/2007 | Mammen et al. | |
| 2007/0249674 A1 | 10/2007 | Bolton et al. | |
| 2007/0276003 A1 | 11/2007 | Mammen et al. | |

FOREIGN PATENT DOCUMENTS

| | | |
|---|---|---|
| EP | 0747355 A1 | 12/1996 |
| WO | 95/06635 A1 | 3/1995 |
| WO | 99/64035 A1 | 12/1999 |
| WO | 02/076933 A1 | 10/2002 |
| WO | 2004/074276 A1 | 9/2004 |
| WO | 2005/051946 A1 | 6/2005 |
| WO | 2005/087735 A1 | 9/2005 |

OTHER PUBLICATIONS

Isogaya et al., "Binding Pockets of the β1- and β2-Adrenergic Receptors for Subtype-Selective Agonists", Molecular Pharmacology, 56: pp. 875-885 (1999).
Naito et al., "Selective Muscarinic Antagonist II. 1) Synthesis and Antimuscarinic Properties of Biphenylylcarbamate Derivatives", Chem. Pharm. Bull., vol. 46, No. 8, pp. 1286-1294 (1998).
"New long acting β agonists", Expert Opin. Ther. Patents, 13(2), pp. 273-277 (2003).

Primary Examiner—Rita J Desai
Assistant Examiner—John Mabry
(74) Attorney, Agent, or Firm—Jeffrey A. Hagenah

(57) ABSTRACT

This invention relates to compounds of formula I:

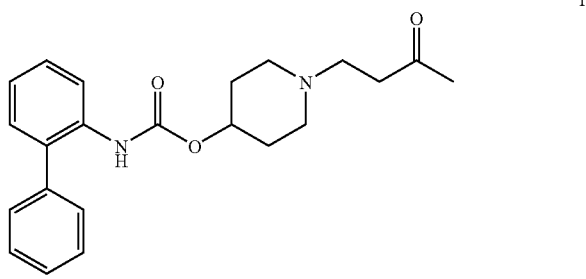

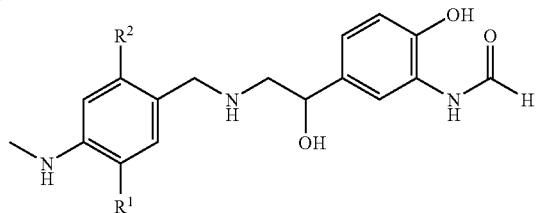

wherein $R^1$ and $R^2$ are as defined in the specification, or a pharmaceutically acceptable salt or solvate or stereoisomer thereof. The invention also relates to pharmaceutical compositions and combinations comprising such compounds, processes and intermediates for preparing such compounds, and methods of using such compound to, for example, treat pulmonary disorders, such as chronic obstructive pulmonary disease and asthma.

11 Claims, No Drawings

DIALKYLPHENYL COMPOUNDS HAVING BETA2 ADRENERGIC RECEPTOR AGONIST AND MUSCARINIC RECEPTOR ANTAGONIST ACTIVITY

CROSS-REFERENCE TO RELATED APPLICATIONS

This application is a divisional of U.S. application Ser. No. 11/789,300, filed Apr. 24, 2007 now U.S. Pat. No. 7,524,965; which application claims the benefit of U.S. Provisional Application No. 60/794,702, filed on Apr. 25, 2006; the entire disclosures of which are incorporated herein by reference in their entirety.

BACKGROUND OF THE INVENTION

1. Field of the Invention

The present invention relates to novel dialkylphenyl compounds having $\beta_2$ adrenergic receptor agonist and muscarinic receptor antagonist activity. This invention also relates to pharmaceutical compositions comprising such compounds, processes and intermediates for preparing such compounds and methods of using such compounds, for example, to treat pulmonary disorders.

2. State of the Art

Pulmonary disorders, such as asthma and chronic obstructive pulmonary disease (COPD), are commonly treated with bronchodilators. One type of bronchodilator used to treat pulmonary disorders consists of $\beta_2$ adrenergic receptor (adrenoceptor) agonists, such as albuterol, formoterol and salmeterol. These compounds are generally administered by inhalation. Another type of bronchodilator consists of muscarinic receptor antagonists (anticholinergic compounds), such as ipratropium and tiotropium. These compounds are also typically administered by inhalation.

Pharmaceutical compositions containing a combination of a $\beta_2$ adrenergic receptor agonist and a muscarinic receptor antagonist are known in the art for use in treating pulmonary disorders. For example, U.S. Pat. No. 6,433,027, issued Aug. 13, 2002, discloses medicament compositions containing a muscarinic receptor antagonist, such as tiotropium bromide, and a $\beta_2$ adrenergic receptor agonist, such as formoterol fumarate.

Additionally, compounds having both $\beta_2$ adrenergic receptor agonist and muscarinic receptor antagonist activity are known in the art. For example, U.S. Pat. No. 7,141,671, issued Nov. 28, 2006, discloses biphenyl compounds having both $\beta_2$ adrenergic receptor agonist and muscarinic receptor antagonist activity. Compounds possessing both $\beta_2$ adrenergic receptor agonist and muscarinic receptor antagonist activity are highly desirable since such compounds provide bronchodilation through two independent modes of action while having single molecule pharmacokinetics.

When treating pulmonary disorders, it is particularly useful to provide therapeutic agents that have a long duration of action, i.e., a duration of at least about 24 hours, when administered by inhalation so that patients only need to administer the therapeutic agent once a day or less. Not all dual-acting compounds disclosed previously in the art possess this desirable property.

Accordingly, a need exists for novel compounds having both $\beta_2$ adrenergic receptor agonist and muscarinic receptor antagonist activity that possess a long duration of action when administered to a patient by inhalation.

SUMMARY OF THE INVENTION

The present invention provides novel dialkylphenyl compounds having both $\beta_2$ adrenergic receptor agonist and muscarinic receptor antagonist activity. Among other properties, a compound of this invention has been found to possess a long duration of action, i.e., a duration of at least about 24 hours, when administered to a mammal by inhalation. Accordingly, the compounds of this invention are expected to be useful and advantageous as therapeutic agents for treating pulmonary disorders.

Accordingly, in one of its composition aspects, the present invention relates to a compound of formula I:

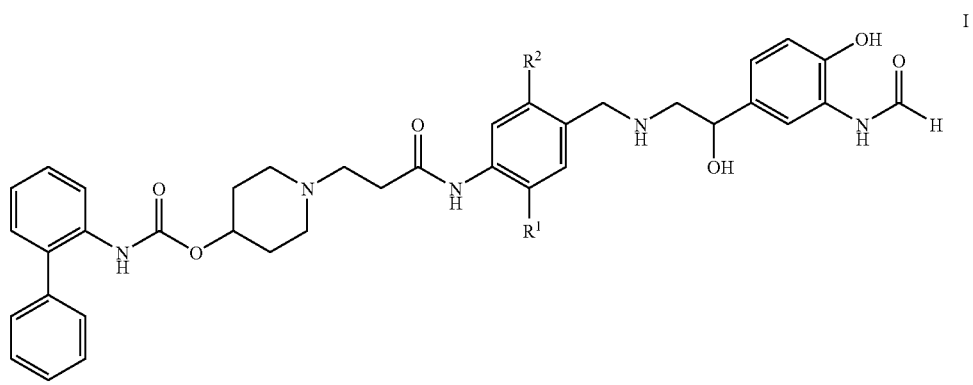

wherein $R^1$ is methyl or ethyl; $R^2$ is methyl or ethyl; or a pharmaceutically acceptable salt or solvate or stereoisomer thereof.

In a particular aspect of this invention, the compound of formula I is a compound having formula II:

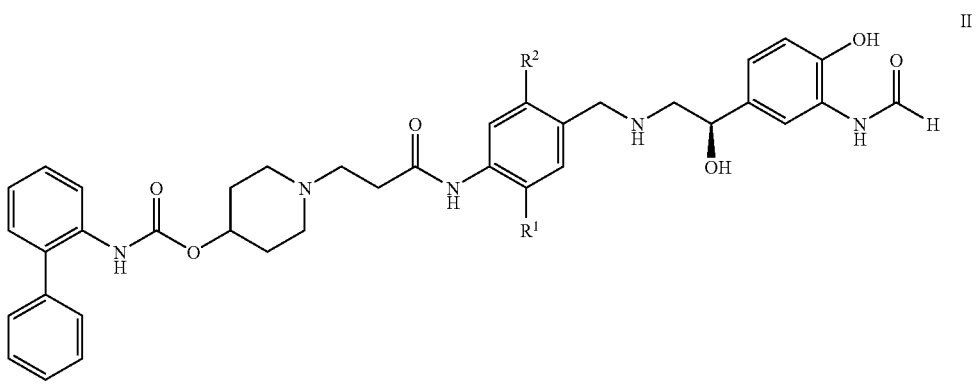

wherein $R^1$ and $R^2$ are as defined herein (including any specific or preferred embodiments); or a pharmaceutically acceptable salt or solvate thereof.

In another of its composition aspects, this invention relates to a pharmaceutical composition comprising a pharmaceutically acceptable carrier and a compound of formula I.

If desired, the compounds of the present invention can be administered in combination with other therapeutic agents, such as a steroidal anti-inflammatory agent. Accordingly, in another of its composition aspects, this invention relates to a pharmaceutical composition comprising (a) a compound of formula I; and (b) a second therapeutic agent. In yet another of its composition aspects, this invention relates to pharmaceutical composition comprising (a) a compound of formula I; (b) a second therapeutic agent; and (c) a pharmaceutically acceptable carrier.

In still another of its composition aspects, this invention relates to a combination of therapeutic agents, the combination comprising (a) a compound of formula I; and (b) a second therapeutic agent. In another of its composition aspects, this invention relates to a combination of pharmaceutical compositions, the combination comprising (a) a first pharmaceutical composition comprising a compound of formula I and a first pharmaceutically acceptable carrier; and (b) a second pharmaceutical composition comprising a second therapeutic agent and a second pharmaceutically acceptable carrier. This invention also relates to a kit containing such pharmaceutical compositions.

Compounds of this invention possess both $\beta_2$ adrenergic receptor agonist activity and muscarinic receptor antagonist activity. Accordingly, the compounds of formula I are expected to be useful as therapeutic agents for treating pulmonary disorders, such as asthma and chronic obstructive pulmonary disease.

Accordingly, in one of its method aspects, this invention relates to a method for treating a pulmonary disorder, the method comprising administering to a patient in need of treatment a therapeutically effective amount of a compound of formula I. This invention also relates to a method of treating chronic obstructive pulmonary disease or asthma, the method comprising administering to a patient a therapeutically effective amount of a compound of formula I. Additionally, in another of its method aspects, this invention relates to a method of producing bronchodilation in a mammal, the method comprising administering to a mammal a bronchodi- lation-producing amount of a compound of formula I. This invention also relates to method of antagonizing a muscarinic receptor and agonizing a $\beta_2$ adrenergic receptor in a mammal, the method comprising administering to the mammal a compound of formula I.

Since compounds of this invention possess both $\beta_2$ adrenergic receptor agonist activity and muscarinic receptor antagonist activity, such compounds are also useful as research tools. Accordingly, in yet another of its method aspects, this invention relates to a method of using a compound of formula I as a research tool, the method comprising conducting a biological assay using a compound of formula I.

The compounds of this invention can also be used to evaluate new chemical compounds. Accordingly, in another of its method aspects, this invention relates to a method of evaluating a test compound in a biological assay, the method comprising: (a) conducting a biological assay with a test compound to provide a first assay value; (b) conducting the biological assay with a compound of formula I to provide a second assay value; wherein step (a) is conducted either before, after or concurrently with step (b); and (c) comparing the first assay value from step (a) with the second assay value from step (b).

This invention also relates to processes and novel intermediates useful for preparing compounds of formula I. Accordingly, in another of its method aspects, this invention relates to a process of preparing a compound of formula I, the process comprising deprotecting a compound of formula 6 (as defined herein) to provide a compound of formula I.

In another of its method aspects, this invention relates to a process of preparing a compound of formula I, the process comprising: (a) reacting a compound of formula 4 with a compound of formula 5 in the presence of a reducing agent to provide a compound of formula 6; and (b) deprotecting the compound of formula 6 to provide a compound of formula I; where compounds 4, 5 and 6 are as defined herein.

In a particular embodiment of this invention, the compounds of formula I are prepared by deprotecting a compound of formula 6, wherein the hydroxyl-protecting group is a silyl group. Accordingly, in yet another of its method aspects, this invention relates to a process of preparing a compound of formula I, the process comprising deprotecting a compound of formula 6a:

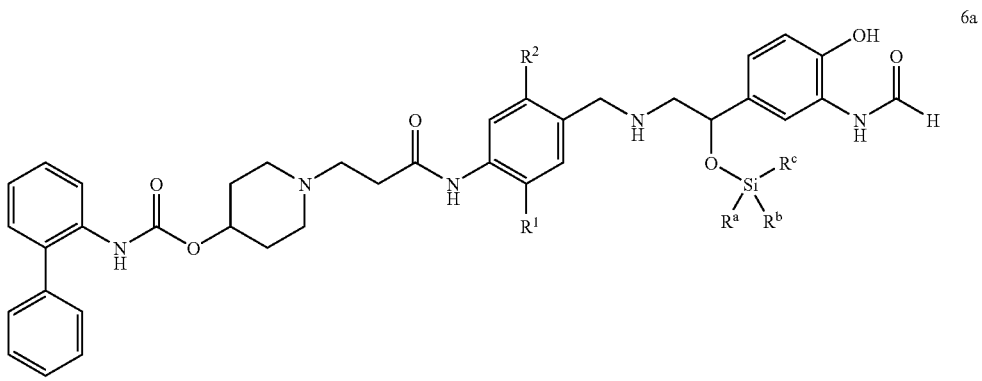

6a wherein $R^a$, $R^b$ and $R^c$ are independently selected from $C_{1-4}$ alkyl, phenyl, —$C_{1-4}$ alkyl-(phenyl), or one of $R^{1a}$, $R^{1b}$ and $R^{1c}$ is —O—($C_{1-4}$ alkyl); to provide a compound of formula I.

In other embodiments, the processes described herein further comprise the step of forming a pharmaceutically acceptable salt of a compound of formula I. In other embodiments, this invention relates to the other processes described herein; and to the product prepared by any of the processes described herein.

In a particular embodiment, this invention relates to a compound of formula III:

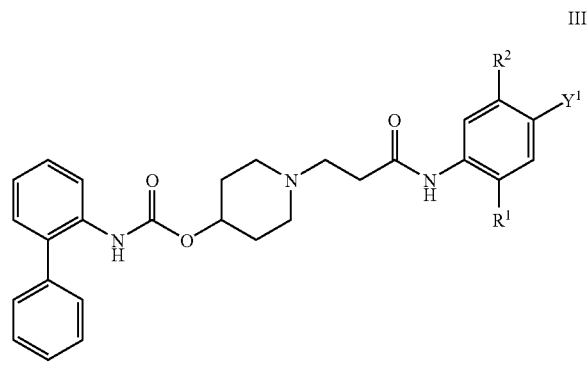

III or a salt or stereoisomer thereof, wherein $Y^1$ is selected from —CHO, —CN, —CH$_2$OH, —CH(OR$^{3a}$)OR$^{3b}$, —C(O)OH, —C(O)OR$^{3c}$, bromo and iodo, where $R^{3a}$ and $R^{3b}$ are selected independently from $C_{1-6}$ alkyl, or $R^{3a}$ and $R^{3b}$ are joined to form $C_{2-6}$ alkylene, $R^{3c}$ is selected from $C_{1-6}$ alkyl; and $R^1$ and $R^2$ are as defined herein (including any specific or preferred embodiments), which compounds are useful as intermediates in preparing compounds of formula I. In a particular embodiment of formula III, $R^1$ and $R^2$ are methyl. In another particular embodiment of formula III, $Y^1$ is —CHO. In still another particular embodiment of formula III, $R^1$ and $R^2$ are methyl and $Y^1$ is —CHO.

This invention also relates to the use of a compound of formula I for therapy. Additionally, the invention relates to the use of a compound of formula I for the manufacture of a medicament for the treatment of a pulmonary disorder; and to the use of a compound of formula I as a research tool. Other aspects and embodiments of this invention are disclosed herein.

DETAILED DESCRIPTION OF THE INVENTION

In one of its composition aspects, this invention relates to novel compounds of formula I. The compounds of formula I contain one or more chiral centers and therefore, this invention is directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions of this invention unless otherwise indicated, provided that the utility of the composition as a whole is not eliminated by the presence of such other isomers.

In particular, compounds of formula I contain a chiral center at the carbon atom indicated by the symbol * in the following partial formula:

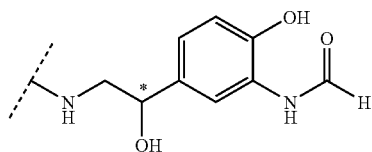

In a particular embodiment of this invention, the carbon atom identified by the symbol * has the (R) configuration. In this embodiment, the compounds of formula I have the (R) configuration at the carbon atom identified by the symbol * or are enriched in a stereoisomeric form having the (R) configuration at this carbon atom.

The compounds of formula I also contain several basic groups (e.g., amino groups) and therefore, the compounds of formula I can exist as the free base or in various salt forms. All such forms are included within the scope of this invention. Furthermore, solvates of compounds of formula I or salts thereof are included within the scope of this invention.

Accordingly, those skilled in the art will recognize that reference to a compound herein, for example, reference to a compound of formula I or compound 6, includes reference to salts and stereoisomers and solvates of that compound unless otherwise indicated.

Additionally, as used herein, the singular forms "a," "an" and "the" include the corresponding plural forms unless the context of use clearly dictates otherwise.

The nomenclature used herein to name the compounds of this invention and intermediates thereof has generally been derived using the commercially available AutoNom software (MDL, San Leandro, Calif.). Typically, compounds of formula I have been named as piperidin-4-yl ester derivatives of biphenyl-2-yl carbamic acid.

Representative Embodiments

The following substituents and values are intended to provide representative examples of various aspects and embodiments of this invention. These representative values are intended to further define and illustrate such aspects and embodiments and are not intended to exclude other embodiments or to limit the scope of this invention. In this regard, the representation that a particular value or substituent is preferred is not intended in any way to exclude other values or substituents from this invention unless specifically indicated.

In one embodiment, $R^1$ is methyl and $R^2$ is methyl.
In another embodiment, $R^1$ is ethyl and $R^2$ is ethyl.
In another embodiment, $R^1$ is methyl and $R^2$ is ethyl.
In another embodiment, $R^1$ is ethyl and $R^2$ is methyl.

Thus, in one of its composition aspects, the present invention relates to compounds of formula I selected from:

biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester (compound IIa);

biphenyl-2-ylcarbamic acid 1-[2-(4-{[(R)-2-(3-formylamino-4-hydroxyphenyl)-2-hydroxyethylamino]methyl}-2,5-diethylphenylcarbamoyl)ethyl]piperidin-4-yl ester (compound IIb);

biphenyl-2-ylcarbamic acid 1-[2-(4-{[(R)-2-(3-formylamino-4-hydroxyphenyl)-2-hydroxyethylamino]methyl}-2-methyl-5-ethylphenylcarbamoyl)ethyl]piperidin-4-yl ester (compound IIc);

biphenyl-2-ylcarbamic acid 1-[2-(4-{[(R)-2-(3-formylamino-4-hydroxyphenyl)-2-hydroxyethylamino]methyl}-2-ethyl-5-methylphenylcarbamoyl)ethyl]piperidin-4-yl ester (compound IId);

or a pharmaceutically acceptable salt thereof.

DEFINITIONS

When describing the compounds, compositions, methods and processes of this invention, the following terms have the following meanings unless otherwise indicated.

The term "alkyl" means a monovalent saturated hydrocarbon group which may be linear or branched. Unless otherwise defined, such alkyl groups typically contain from 1 to 10 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

When a specific number of carbon atoms is intended for a particular term used herein, the number of carbon atoms is shown preceding the term. For example, the term "$C_{1-3}$ alkyl" means an alkyl group having from 1 to 3 carbon atoms wherein the carbon atoms are in any chemically-acceptable configuration.

The term "alkylene" means a divalent saturated hydrocarbon group that may be linear or branched. Unless otherwise defined, such alkylene groups typically contain from 1 to 10 carbon atoms. Representative alkylene groups include, by way of example, methylene, ethane-1,2-diyl ("ethylene"), propane-1,2-diyl, propane-1,3-diyl, butane-1,4-diyl, pentane-1,5-diyl and the like.

The term "amino-protecting group" means a protecting group suitable for preventing undesired reactions at an amino group. Representative amino-protecting groups include, but are not limited to, tert-butoxycarbonyl (BOC), trityl (Tr), benzyloxycarbonyl (Cbz), 9-fluorenylmethoxycarbonyl (Fmoc), benzyl, formyl, trimethylsilyl (TMS), tert-butyldimethylsilyl (TBS), and the like.

The term "carboxy-protecting group" means a protecting group suitable for preventing undesired reactions at a carboxy group. Representative carboxy-protecting groups include, but are not limited to, esters, such as methyl, ethyl, tert-butyl, benzyl (Bn), p-methoxybenzyl (PMB), 9-fluorenylmethyl (Fm), trimethylsilyl (TMS), tert-butyldimethylsilyl (TBS), diphenylmethyl (benzhydryl, DPM) and the like.

The term "compound of the invention" or "compound of formula I" or "compound of formula II" as used herein means the specified compound(s) or a pharmaceutically acceptable salt or solvate or stereoisomer thereof unless otherwise indicated.

The term "halo" means fluoro, chloro, bromo and iodo.

The term "hydroxyl-protecting group" means a protecting group suitable for preventing undesirable reactions at a hydroxyl group. Representative hydroxyl-protecting groups include, but are not limited to, silyl groups including tri($C_{1-6}$ alkyl)silyl groups, such as trimethylsilyl (TMS), triethylsilyl (TES), tert-butyldimethylsilyl (TBS) and the like; esters (acyl groups) including $C_{1-6}$ alkanoyl groups, such as formyl, acetyl and the like; arylmethyl groups, such as benzyl (Bn), p-methoxybenzyl (PMB), 9-fluorenylmethyl (Fm), diphenylmethyl (benzhydryl, DPM) and the like. Additionally, two hydroxyl groups can also be protected as an alkylidene group, such as prop-2-ylidine, formed, for example, by reaction with a ketone, such as acetone.

The term "leaving group" means a functional group or an atom that can be displaced by another functional group or atom in a substitution reaction, such as a nucleophilic substitution reaction. By way of example, representative leaving groups include, but are not limited to, chloro, bromo and iodo groups; sulfonic ester groups, such as mesylate, tosylate, brosylate, nosylate and the like; and acyloxy groups, such as acetoxy, trifluoroacetoxy and the like.

The term "mass median diameter" or "MMD" when used to refer to particles means the diameter such that half the mass of the particles is contained in particles with larger diameter and half is contained in particles with smaller diameter.

The term "micronized" or "in micronized form" means particles in which at least about 90 percent of the particles have a diameter of less than about 10 μm unless otherwise indicated.

The term "or a pharmaceutically acceptable salt or solvate or stereoisomer thereof" as used herein is intended to include all permutations of salts, solvates and stereoisomers, such as a solvate of a pharmaceutically acceptable salt of a stereoisomer of a compound of formula I.

The term "pharmaceutically acceptable salt" means a salt that is acceptable for administration to a patient, such as a mammal (e.g., salts having acceptable mammalian safety for a given dosage regime). Representative pharmaceutically acceptable salts include salts of acetic, ascorbic, benzenesulfonic, benzoic, camphosulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "protected derivatives thereof" means a derivative of the specified compound in which one or more functional groups of the compound are protected or blocked from undergoing undesired reactions with a protecting or blocking group. Functional groups that may be protected include, by way of example, carboxy groups, amino groups, hydroxyl groups, thiol groups, carbonyl groups and the like. Suitable protecting groups for such functional groups are well known to those of ordinary skill in the art as exemplified by the teachings in T. W. Greene and G. M. Wuts, *Protecting Groups in Organic Synthesis*, Third Edition, Wiley, New York, 1999, and references cited therein.

The term "salt thereof" means a compound formed when the hydrogen of an acid is replaced by a cation, such as a metal cation or an organic cation and the like. In the present invention, the cation typically comprises a protonated form of a compound of formula I, i.e. where one or more amino groups having been protonated by an acid. Preferably, the salt is a pharmaceutically acceptable salt, although this is not required for salts of intermediate compounds that are not intended for administration to a patient.

The term "solvate" means a complex or aggregate formed by one or more molecules of a solute, i.e. a compound of formula I or a pharmaceutically acceptable salt thereof, and one or more molecules of a solvent. Such solvates are typically crystalline solids having a substantially fixed molar ratio of solute and solvent. Representative solvents include, by way of example, water, methanol, ethanol, isopropanol, acetic acid and the like. When the solvent is water, the solvate formed is a hydrate.

The term "therapeutically effective amount" means an amount sufficient to effect treatment when administered to a patient in need of treatment.

The term "treating" or "treatment" as used herein means the treating or treatment of a disease or medical condition (such as COPD or asthma) in a patient, such as a mammal (particularly a human) that includes:

(a) preventing the disease or medical condition from occurring, i.e., prophylactic treatment of a patient;
(b) ameliorating the disease or medical condition, i.e., eliminating or causing regression of the disease or medical condition in a patient;
(c) suppressing the disease or medical condition, i.e., slowing or arresting the development of the disease or medical condition in a patient; or
(d) alleviating the symptoms of the disease or medical condition in a patient.

All other terms used herein are intended to have their ordinary meaning as understood by those of ordinary skill in the art to which they pertain.

General Synthetic Procedures

The compounds of this invention can be prepared from readily available starting materials using the following general methods and procedures or by using other information readily available to or known by those of ordinary skill in the art. Although the following procedures may illustrate a particular embodiment or aspect of the present invention, those skilled in the art will recognize that other embodiments or aspects of the present invention can be prepared using the same or similar methods or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. While optimum reaction conditions will typically vary depending on various reaction parameters such as the reactants, solvents and quantities used, those of ordinary skill in the art can readily determine suitable reaction conditions using routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions and reagents for protection and deprotection of such functional groups are well known in the art. Protecting groups other than those illustrated in the procedures described herein may be used, if desired.

In one embodiment, the compounds of formula I are synthesized as illustrated in Scheme I:

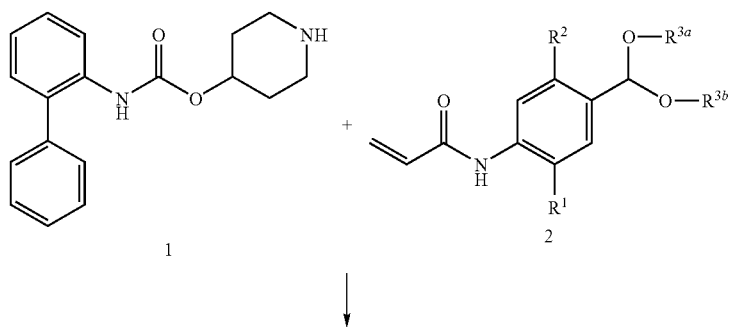

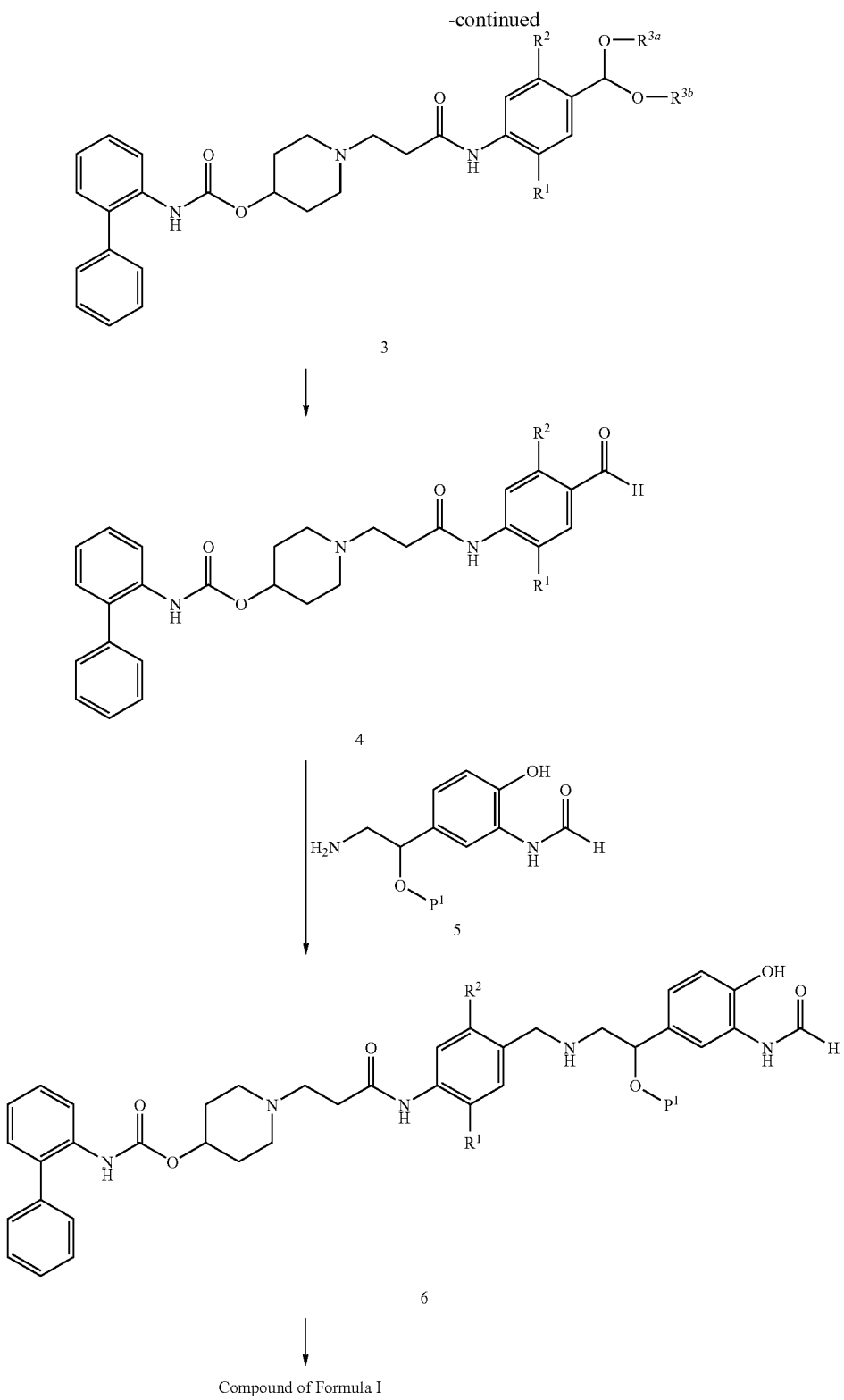

wherein $P^1$ is a hydroxyl-protecting group; and $R^{3a}$ and $R^{3b}$ are selected independently from $C_{1-6}$ alkyl, or $R^{3a}$ and $R^{3b}$ are joined to form $C_{2-6}$ alkylene.

As shown in Scheme I, compound 1 can be reacted with about 0.95 to about 1.05 molar equivalents of compound 2 to provide compound 3. This Michael reaction is typically conducted at a temperature ranging from about 0° C. to about 75° C., typically about 40° C. to about 45° C., for about 8 to about 24 hours or until the reaction is substantially complete. Generally, this reaction is conducted in a suitable diluent, such as dichloromethane or mixtures of dichloromethane and methanol or ethanol, and the like. Upon completion of the reaction, the product is typically isolated using conventional procedures, such as extraction, recrystallization, chromatography and the like. Alternatively, the reaction mixture containing compound 3 can be used directly in the next step of the synthesis.

Compound 3 is then reacted with aqueous acid to hydrolyze the acetal group and provide aldehyde compound 4. Any suitable acid can be employed in this reaction including, by way of example, hydrochloric acid, sulfuric acid, methanesulfonic acid, p-toluenesulfonic acid and the like. The hydrolysis reaction is typically conducted at a temperature ranging from about 0° C. to about 30° C., typically about 20° C. to about 25° C., for about 1 to about 6 hours or until the reaction is substantially complete. Generally, this reaction is conducted in a suitable diluent, such as methanol, ethanol, isopropanol, dichloromethane/ethanol, acetonitrile and the like. Upon completion of the reaction, the product is typically isolated using conventional procedures, such as extraction, recrystallization, chromatography and the like.

Compound 4 is then reacted with about 0.95 to about 1.5 molar equivalents of compound 5 in the presence of a reducing agent to afford compound 6. Any suitable reducing agent may be used in this reaction including, by way of illustration, a metal hydride reagent, such as sodium borohydride, sodium triacetoxyborohydride, sodium cyanoborohydride and the like, or hydrogen and a metal catalyst, such as palladium on carbon, and the like. This reductive alkylation reaction is typically conducted at a temperature ranging from about −20° C. to about 30° C., typically about 0° C. to about 5° C., for about 1 to about 6 hours or until the reaction is substantially complete. Generally, this reaction is conducted in a suitable diluent and a protic solvent, such as dichloroethane and methanol, and the like. Upon completion of the reaction, the product is typically isolated using conventional procedures, such as extraction, recrystallization, chromatography and the like.

Compound 6 is then deprotected to provide a compound of formula I. The particular conditions used to deprotect compound 6 will depend on the protecting group employed. For example, when $P^1$ is a silyl protecting group (i.e., a compound of formula 6a as defined herein), such as tert-butyldimethylsilyl, tert-butyldiphenylsilyl, diphenylmethylsilyl, di-tert-buylmethylsilyl, tert-butoxydiphenylsilyl and the like, this deprotection reaction is typically conducted by contacting compound 6a with a source of fluoride ion. In a particular embodiment, the source of fluoride ion is triethylamine trihydrofluoride. Other suitable sources of fluoride ion include tetrabutylammonium fluoride, potassium fluoride with 18-crown-6, hydrogen fluoride, pyridine hydrofluoride, and the like. This reaction is typically conducted at a temperature ranging from about 0° C. to about 50° C., typically about 10° C. to about 25° C., for about 24 to about 72 hours or until the reaction is substantially complete. Generally, this reaction is conducted in a suitable diluent, such as dichloroethane and the like. Upon completion of the reaction, the product is typically isolated using conventional procedures, such as extraction, recrystallization, chromatography and the like.

Compound 1 is known in the art or can be prepared from commercially available starting materials and reagents using known procedures. See, for example, U.S. Patent Application Publication No. U.S. 2004/0167167 A1 and R. Naito et al., Chem. Pharm. Bull., 46(8) 1286-1294 (1998). By way of example, compound 1 can be prepared as illustrated in Scheme II:

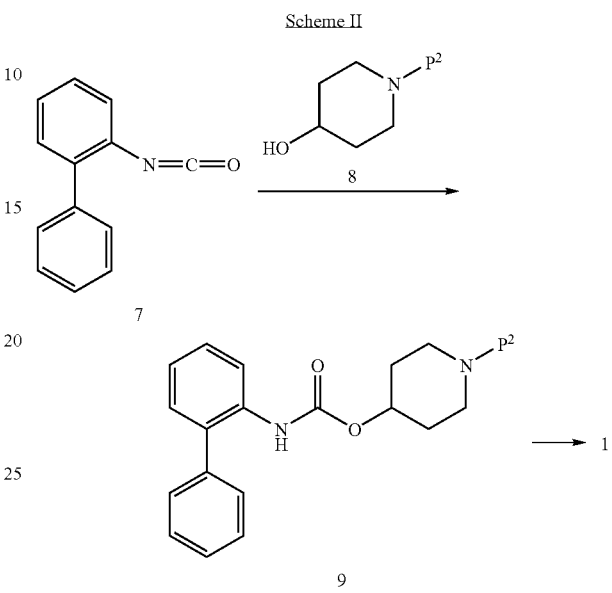

As shown in Scheme II, biphenyl-2-isocyanate (7) is reacted with an N-protected 4-hydroxypiperidine 8, where $P^2$ is an amino-protecting group such as benzyl, to provide carbamate intermediate 9. This reaction is typically conducted at a temperature ranging from about 20° C. to about 100° C., typically about 60° C. to about 80° C., for about 6 to about 24 hours or until the reaction is substantially complete. If desired, this reaction can be conducted in a suitable diluent, such as dichloromethane, toluene and the like. Alternatively, this reaction can be conducted in the absence of a diluent. Upon completion of the reaction, the product 9 is typically isolated using conventional procedures, such as extraction, recrystallization, chromatography and the like. Alternatively, the reaction mixture containing compound 9 is used directly in the next step of the synthesis.

The amino-protecting group, $P^2$, is then removed from compound 9 using conventional procedures to afford compound 1. For example, when $P^2$ is a benzyl group, compound 9 can be deprotected using hydrogen or ammonium formate, in the presence of a catalyst, such as a palladium catalyst. Representative catalysts include, by way of illustration, palladium on carbon, palladium hydroxide on carbon and the like. This reaction is typically conducted at a temperature ranging from about 20° C. to about 50° C., typically about 40° C., for about 6 to about 24 hours or until the reaction is substantially complete. Generally, this reaction is conducted in a suitable diluent, such as methanol, ethanol, isopropanol and the like. Upon completion of the reaction, compound 1 is typically isolated using conventional procedures, such as extraction, recrystallization, chromatography and the like.

Compounds of formula 2 are known in the art or can be prepared from commercially available starting materials and reagents using known procedures. By way of illustration, compounds of formula 2 can be prepared as shown in Scheme III:

Scheme III

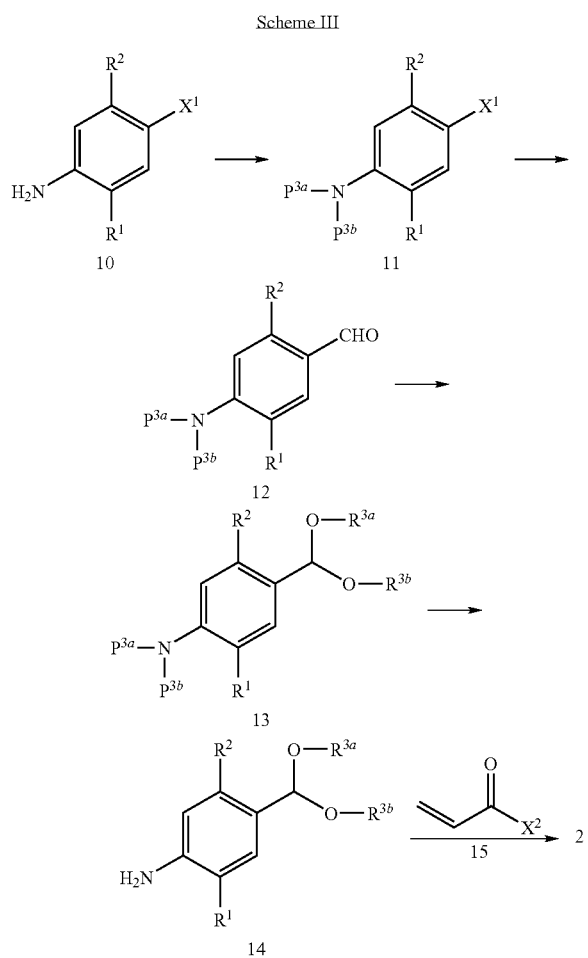

As shown in Scheme III, an aniline compound of formula 10, where $X^1$ is bromo or iodo, is first protected at the amino group to provide a compound of formula 11, where $P^{3a}$ is an amino-protecting group and $P^{3b}$ is hydrogen or an amino-protecting group. Any suitable amino-protecting group may be used, such as benzyl, 4-methoxybenzyl, trifluoroacetyl and the like. For example, a compound of formula 10 can be reacted with about 2 or more molar equivalents, preferably about 2.5 to about 3.0 molar equivalents, of a benzyl halide, such as benzyl chloride, bromide or iodide, to afford compound 11 where $P^{3a}$ and $P^{3b}$ are both benzyl. This reaction is typically conducted at a temperature ranging from about 0° C. to about 50° C., typically about 30° C., for about 18 to about 24 hours or until the reaction is substantially complete. Generally, this reaction is conducted in a suitable diluent, such as methanol, ethanol, isopropanol and the like. Typically, this reaction is also conducted in the presence of a suitable base, such as potassium carbonate, sodium carbonate and the like. Upon completion of the reaction, compound 11 is typically isolated using conventional procedures, such as extraction, recrystallization, chromatography and the like.

Representative compounds of formula 10 that can be employed in this reaction include 2,5-dimethyl-4-iodoaniline, 2,5-diethyl-4-iodoaniline, 2-ethyl-4-iodo-5-methylaniline, 5-ethyl-4-iodo-2-methylaniline, 4-bromo-2,5-dimethylaniline, 4-bromo-2,5-diethylaniline, 4-bromo-2-ethyl-5-methylaniline, 4-bromo-5-ethyl-2-methylaniline and the like. Such compounds are commercially available (for example, from Spectra Group Limited, Inc., Millbury, Ohio) or can be prepared from commercially available starting materials and reagents using conventional procedures.

Compound 11 is then contacted with about 1 to about 2 molar equivalents of an alkyl lithium reagent, such as n-butyllithium or tert-butyllithium, to form the corresponding anion in which the $X^1$ group has been exchanged for lithium. This reaction is typically conducted at a temperature ranging from about −70° C. to about 0° C., typically about −20° C., for about 0.25 to about 1 hour or until the reaction is substantially complete. Generally, this reaction is conducted in a suitable diluent, such as toluene, xylene, tetrahydrofuran and the like.

The resulting lithium anion is not isolated, but is reacted in situ with a molar excess of N,N-dimethylformamide to provide compound 12. Generally, about 2 to about 4 molar equivalents of N,N-dimethylformamide are used. This reaction is typically conducted at a temperature ranging from about −70° C. to about 0° C., typically about −20° C. to about 0° C., for about 0.5 to about 2 hours or until the reaction is substantially complete. Upon completion of the reaction, compound 12 is typically isolated using conventional procedures, such as extraction, recrystallization, chromatography and the like.

The aldehyde group of compound 12 is then protected as an acetal by reacting compound 12 with an alcohol or a diol in the presence of an acid catalyst. Any suitable alcohol or diol can be used in this reaction. For example, representative alcohols and diols include methanol, ethanol, n-propanol, ethylene glycol, propylene glycol and the like. Generally, a molar excess of the alcohol or diol are employed in this reaction, preferably about 2 to about 4 molar equivalents.

Any suitable acid catalyst may be used in this reaction to facilitate formation of the acetal. Representative acid catalysis include, by way of example, p-toluenesulfonic acid, benzenesulfonic acid, hydrochloric acid and the like.

The reaction is typically conducted at a temperature ranging from about 50° C. to about 100° C., typically about 60° C. to about 80° C., for about 12 to about 24 hours or until the reaction is substantially complete. Generally, this reaction is conducted in a suitable diluent, such as toluene, xylene and the like. Typically, the reaction is conducted in a manner which allows the water produced to be removed, such as by azeotropic distillation or by the use of molecular sieves. Upon completion of the reaction, compound 13 is typically isolated using conventional procedures, such as extraction, recrystallization, chromatography and the like. Alternatively, the reaction mixture containing compound 13 can be used directly in the next step of the synthesis.

After formation of the acetal, the amino group of compound 13 is deprotected using standard reagents and conditions to form compound 14. For example, if $P^{3a}$ and $P^{3b}$ are benzyl groups, compound 13 can be deprotected using hydrogen and a catalyst, such as a palladium catalyst. Representative catalysts include, by way of example, palladium on carbon, palladium hydroxide on carbon, and the like. This reaction is typically conducted at a temperature ranging from about 20° C. to about 50° C., typically about 25° C. to about 30° C., for about 4 to about 12 hours or until the reaction is substantially complete. Generally, this reaction is conducted in a suitable diluent, such as methanol, ethanol, ethanol/ethyl acetate mixtures and the like. Upon completion of the reaction, compound 14 is typically isolated using conventional procedures, such as extraction, recrystallization, chromatography and the like.

Compound 14 is then reacted with an acryloyl halide 15, where $X^2$ is chloro, bromo or iodo, to form compound 2. This reaction is typically conducted at a temperature ranging from about −20° C. to about 25° C., typically about 0° C. to about 5° C., for about 0.5 to about 6 hours or until the reaction is substantially complete. Generally, this reaction is conducted in a suitable diluent, such as dichloromethane and the like, in the presence of a suitable base, such as diisopropylethylamine, triethylamine and the like. Generally, about 1 to 1.2 molar equivalents of the acryloyl halide and about 1 to about 2 molar equivalent of the base are used in this reaction. Upon completion of the reaction, compound 2 is typically isolated using conventional procedures, such as extraction, recrystallization, chromatography and the like.

Compounds of formula 5 are known in the art or can be prepared from commercially available starting materials and reagents using known procedures. By way of illustration, compounds of formula 5 can be prepared as shown in Scheme IV:

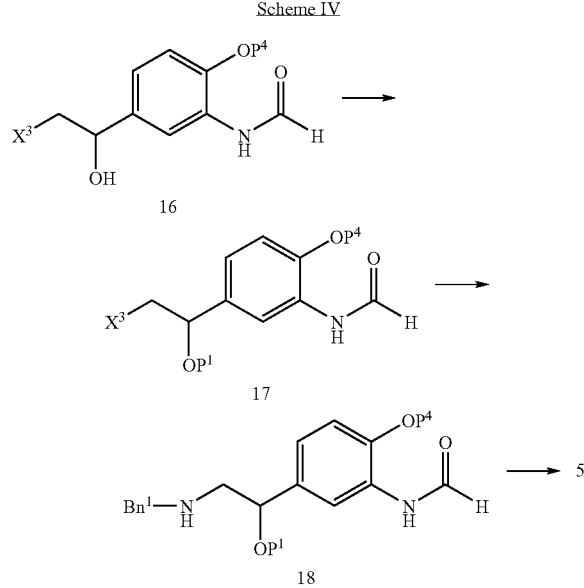

As illustrated in Scheme IV, compounds of formula 5 can be prepared from compounds of formula 16, where $P^4$ is a hydroxyl-protecting group, such as benzyl, and $X^3$ is a leaving group, such as chloro, bromo or iodo. Compounds of formula 16 are known in the art. For example, U.S. Pat. No. 6,268,533 B1, issued Jul. 31, 2001; and R. Hett et al., *Organic Process Research & Development* 1998, 2, 96-99; describe the preparation of N-[2-benzyloxy-5-((R)-2-bromo-1-hydroxyethyl)phenyl]formamide (i.e., the (R) enantiomer of compound 16, where $P^4$ is benzyl and $X^3$ is bromo) starting from 2-bromo-4'-benzyloxy-3'-nitroacetophenone, the synthesis of which is described in K. Murase et al., *Chem. Pharm. Bull.*, 25(6) 1368-1377 (1977). If desired, the racemic form of compound 16 can be prepared by using a non-chiral reducing agent, such as borane dimethylsulfide complex, to reduce 2-bromo-4'-benzyloxy-3'-nitroacetophenone.

The hydroxyl group of compound 16 is protected using conventional procedures and reagents to provide compound 17, where $P^1$ is a hydroxyl-protecting group. In a particular embodiment, the hydroxyl-protecting group is a silyl protecting group, such as dimethylisopropylsilyl, diethylisopropylsilyl, dimethylhexylsilyl, tert-butyldimethylsilyl, tert-butyldiphenylsilyl, diphenylmethylsilyl and the like. For example, compound 16 can be reacted with about 0.95 to about 1.2 molar equivalent of tert-butyldimethylsilyl chloride in the presence of about 1.1 to about 1.3 molar equivalents of imidazole to provide compound 17 where $P^1$ is tert-butyldimethylsilyl. This reaction is typically conducted at a temperature ranging from about 0° C. to about 50° C., typically at room temperature, for about 24 to about 48 hours or until the reaction is substantially complete. Generally, this reaction is conducted in a suitable diluent, such as N,N-dimethylformamide and the like. Upon completion of the reaction, compound 17 is typically isolated using conventional procedures, such as extraction, chromatography and the like. By way of further illustration, the synthesis of N-{2-benzyloxy-5-[(R)-2-bromo-1-(tert-butyldimethylsilanyloxy)ethyl]phenyl}formamide is described in Example 2 of U.S. Patent Publication No. US 2004/0248985 A1, published Dec. 9, 2004.

Compound 17 is then reacted with a benzyl amine (i.e., $Bn^1$—$NH_2$) to afford compound 18, where $Bn^1$ is an unsubstituted benzyl group or a substituted benzyl group having 1 to 3 substituents on the phenyl ring of the benzyl group selected independently from $C_{1-4}$ alkyl or $C_{1-4}$ alkoxy. Representative benzyl amines include, benzylamine, 3,4-dimethoxybenzylamine, 4-methoxybenzylamine, 4-methylbenzylamine and the like. This reaction is typically conducted by contacting compound 17 with about 2 to about 4 molar equivalents of the benzyl amine at a temperature ranging from about 40° C. to about 100° C., typically from about 80° C. to about 90° C., for about 5 to about 24 hours or until the reaction is substantially complete. Generally, this reaction is conducted in a suitable diluent, such as N-methyl-2-pyrrolidone (NMP) and the like. Upon completion of the reaction, compound 18 is typically isolated using conventional procedures, such as extraction, chromatography, recrystallization and the like.

Removal of the benzyl group, $Bn^1$, and $P^4$ using conventional procedures and reagents then affords compound 5. In one embodiment, both $Bn_1$ and $P^4$ are benzyl groups that are removed in the same reaction mixture. Typically, this reaction is conducted by contacting compound 5 with hydrogen in the presence of a catalyst, such as a palladium catalyst. Representative catalysts include palladium hydroxide on carbon, palladium on carbon, and the like. Generally, this debenzylation reaction is conducted in the presence of an acid, such as acetic acid, formic acid and the like. This reaction is typically conducted at a temperature ranging from about 10° C. to about 50° C., typically at room temperature, for about 6 to about 24 hours or until the reaction is substantially complete. Generally, this reaction is conducted in a suitable diluent, such as methanol, ethanol and the like. Upon completion of the reaction, compound 5 is typically isolated using conventional procedures, such as extraction, chromatography and the like. In a particular embodiment, compound 5 is isolated as the acetic acid salt.

Those of ordinary skill in the art will recognize that the compounds of formula I can also be prepared by other synthetic procedures. For example, the particular order in which the synthetic steps are conducted can be changed or different intermediates can be employed. By way of illustration, compounds of formula III:

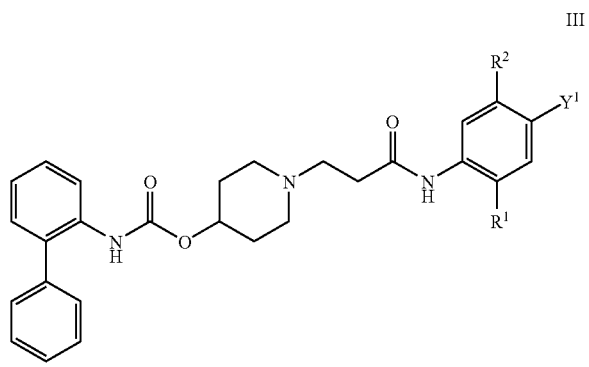

where $Y^1$ is —CN, —C(O)OH or —C(O)OR$^{3c}$ can be reduced using conventional procedures and reagents to provide aldehyde 4 (i.e., where $Y^1$ is —CHO). Additionally, such compounds can be reduced to the alcohol, i.e., where $Y^1$ is —CH$_2$OH, and the alcohol can then be oxidized using standard procedures and reagents to provide aldehyde 4 (i.e., where $Y^1$ is —CHO).

If desired, pharmaceutically acceptable salts of the compounds of formula I can be prepared by contacting the free base form of a compound of formula I with a pharmaceutically acceptable acid.

Further details regarding specific reaction conditions and other procedures for preparing representative compounds of this invention or intermediates thereof are described in the Examples set forth below.

Pharmaceutical Compositions Combinations and Formulations

The compounds of this invention are typically administered to a patient in the form of a pharmaceutical composition or formulation. Such pharmaceutical compositions may be administered to the patient by any acceptable route of administration including, but not limited to, inhaled, oral, nasal, topical (including transdermal) and parenteral modes of administration. It will be understood that any form of a compound of this invention, (i.e., free base, pharmaceutically acceptable salt, solvate, etc.) that is suitable for a particular mode of administration can be used in the pharmaceutical compositions discussed herein.

Accordingly, in one of its compositions aspects, this invention relates to a pharmaceutical composition comprising a pharmaceutically acceptable carrier or excipient and a compound of formula I. Optionally, such pharmaceutical compositions may contain other therapeutic and/or formulating agents if desired.

The pharmaceutical compositions of this invention typically contain a therapeutically effective amount of a compound of formula I. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, the pharmaceutical composition will contain from about 0.01 to about 95 percent by weight of the therapeutic agent; including, from about 0.01 to about 30 percent by weight; such as from about 0.01 to about 10 percent by weight of the therapeutic agent.

Any conventional carrier or excipient may be used in the pharmaceutical compositions of this invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those of ordinary skill in the pharmaceutical arts.

The carriers or excipients used in the pharmaceutical compositions of this invention are commercially available. For example, such materials can be purchased from Sigma (St. Louis, Mo.). By way of further illustration, conventional formulation techniques are well known to those of ordinary skill in the art as exemplified by the teachings in *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) compressed propellant gases, such as chlorofluorocarbons and hydrofluorocarbons; and (22) other non-toxic compatible substances employed in pharmaceutical compositions.

The pharmaceutical compositions of this invention are typically prepared by thoroughly and intimately mixing or blending a compound of the invention with a pharmaceutically acceptable carrier and any optional ingredients. If necessary or desired, the resulting uniformly blended mixture can then be shaped or loaded into tablets, capsules, pills, canisters, cartridges, dispensers and the like using conventional procedures and equipment.

In one embodiment, the pharmaceutical compositions of this invention are suitable for inhaled administration. Suitable pharmaceutical compositions for inhaled administration will typically be in the form of an aerosol or a powder. Such compositions are generally administered using well-known delivery devices, such as a nebulizer inhaler, a metered-dose inhaler (MDI), a dry powder inhaler (DPI) or a similar delivery device.

In a specific embodiment of this invention, the pharmaceutical composition comprising the therapeutic agent is administered by inhalation using a nebulizer inhaler. Such nebulizer devices typically produce a stream of high velocity air that causes the pharmaceutical composition comprising the therapeutic agent to spray as a mist that is carried into the patient's respiratory tract. Accordingly, when formulated for use in a nebulizer inhaler, the therapeutic agent is typically dissolved in a suitable carrier to form a solution. Alternatively, the therapeutic agent can be micronized and combined with a suitable carrier to form a suspension of micronized particles. Nebulizer devices suitable for administering therapeutic agents by inhalation are well known to those of ordinary skill in the art or such devices are commercially available. For example, representative nebulizer devices or products include the Respimat Softmist Inhalaler (Boehringer Ingelheim); the AERxPulmonary Delivery System (Aradigm Corp.); the PARI LC Plus Reusable Nebulizer (Pari GmbH); and the like.

A representative pharmaceutical composition for use in a nebulizer inhaler comprises an isotonic aqueous solution comprising from about 0.05 µg/mL to about 10 mg/mL of a compound of formula I. In one embodiment, such a solution has a pH of about 4 to about 6.

In another specific embodiment of this invention, the pharmaceutical composition comprising the therapeutic agent is administered by inhalation using a dry powder inhaler. Such dry powder inhalers typically administer the therapeutic agent as a free-flowing powder that is dispersed in a patient's air-stream during inspiration. In order to achieve a free-flowing powder, the therapeutic agent is typically formulated with a suitable excipient such as lactose, starch, mannitol, dextrose, polylactic acid (PLA), polylactide-co-glycolide (PLGA) or combinations thereof. Typically, the therapeutic agent is micronized and combined with a suitable carrier to form a blend suitable for inhalation. Accordingly, in one embodiment of the invention, the compound of formula I is in micronized form.

A representative pharmaceutical composition for use in a dry powder inhaler comprises dry milled lactose and micronized particles of a compound of formula I.

Such a dry powder formulation can be made, for example, by combining the lactose with the therapeutic agent and then dry blending the components. Alternatively, if desired, the therapeutic agent can be formulated without an excipient. The pharmaceutical composition is then typically loaded into a dry powder dispenser, or into inhalation cartridges or capsules for use with a dry powder delivery device.

Dry powder inhaler delivery devices suitable for administering therapeutic agents by inhalation are well known to those of ordinary skill in the art or such devices are commercially available. For example, representative dry powder inhaler delivery devices or products include Aeolizer (Novartis); Airmax (IVAX); ClickHaler (Innovata Biomed); Diskhaler (GlaxoSmithKline); Diskus/Accuhaler (GlaxoSmithKline); Easyhaler (Orion Pharma); Eclipse (Aventis); FlowCaps (Hovione); Handihaler (Boehringer Ingelheim); Pulvinal (Chiesi); Rotahaler (GlaxoSmithKline); SkyeHaler/Certihaler (SkyePharma); Twisthaler (Schering-Plough); Turbuhaler (AstraZeneca); Ultrahaler (Aventis); and the like.

In yet another specific embodiment of this invention, the pharmaceutical composition comprising the therapeutic agent is administered by inhalation using a metered-dose inhaler. Such metered-dose inhalers typically discharge a measured amount of the therapeutic agent using a compressed propellant gas. Accordingly, pharmaceutical compositions administered using a metered-dose inhaler typically comprise a solution or suspension of the therapeutic agent in a liquefied propellant. Any suitable liquefied propellant may be employed including chlorofluorocarbons, such as $CCl_3F$, and hydrofluoroalkanes (HFAs), such as 1,1,1,2-tetrafluoroethane (HFA 134a) and 1,1,1,2,3,3,3-heptafluoro-n-propane, (HFA 227). Due to concerns about chlorofluorocarbons affecting the ozone layer, formulations containing HFAs are generally preferred. Additional optional components of HFA formulations include co-solvents, such as ethanol or pentane, and surfactants, such as sorbitan trioleate, oleic acid, lecithin, and glycerin.

A representative pharmaceutical composition for use in a metered-dose inhaler comprises from about 0.01% to about 5% by weight of a compound of formula I; from about 0% to about 20% by weight ethanol; and from about 0% to about 5% by weight surfactant; with the remainder being an HFA propellant.

Such compositions are typically prepared by adding chilled or pressurized hydrofluoroalkane to a suitable container containing the therapeutic agent, ethanol (if present) and the surfactant (if present). To prepare a suspension, the therapeutic agent is micronized and then combined with the propellant. The formulation is then loaded into an aerosol canister, which forms a portion of a metered-dose inhaler device.

Metered-dose inhaler devices suitable for administering therapeutic agents by inhalation are well known to those of ordinary skill in the art or such devices are commercially available. For example, representative metered-dose inhaler devices or products include AeroBid Inhaler System (Forest Pharmaceuticals); Atrovent Inhalation Aerosol (Boehringer Ingelheim); Flovent (GlaxoSmithKline); Maxair Inhaler (3M); Proventil Inhaler (Schering); Serevent Inhalation Aerosol (GlaxoSmithKline); and the like.

In another embodiment, the pharmaceutical compositions of this invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of this invention will typically comprise a compound of the present invention as the active ingredient and one or more pharmaceutically acceptable carriers, such as sodium citrate or dicalcium phosphate. Optionally or alternatively, such solid dosage forms may also comprise: (1) fillers or extenders, such as starches, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical compositions of this invention. Examples of pharmaceutically acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid!methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of this invention may be packaged in a unit dosage form. The term "unit dosage form" means a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like.

The compounds of this invention can also be administered transdermally using known transdermal delivery systems and excipients. For example, a compound of this invention can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

Additionally, the compounds of this invention can be administered parenterally, i.e., intravenously, subcutaneously or intramuscularly. For parenteral administration, a compound of formula I is typically dissolved in a carrier acceptable for parenteral administration, such as sterile water, saline, vegetable oil and the like. By way of illustration, an intravenous composition typically comprises a sterile aqueous solution of a compound of formula I, wherein the solution has a pH in the range of about 4 to about 7.

If desired, the compounds of this invention may be administered in combination with one or more other therapeutic agents. In this embodiment, a compound of this invention is either physically mixed with the other therapeutic agent to form a composition containing both agents; or each agent is present in separate and distinct compositions which are administered to the patient simultaneously or sequentially.

For example, a compound of formula I can be combined with second therapeutic agent using conventional procedures and equipment to form a composition comprising a compound of formula I and a second therapeutic agent. Additionally, the therapeutic agents may be combined with a pharmaceutically acceptable carrier to form a pharmaceutical composition comprising a compound of formula I, a second therapeutic agent and a pharmaceutically acceptable carrier. In this embodiment, the components of the composition are typically mixed or blended to create a physical mixture. The physical mixture is then administered in a therapeutically effective amount using any of the routes described herein.

Alternatively, the therapeutic agents may remain separate and distinct before administration to the patient. In this embodiment, the therapeutic agents are not physically mixed together before administration but are administered simultaneously or sequentially as separate compositions. For example, a compound of formula I can be administered by inhalation simultaneously or sequentially with another therapeutic agent using an inhalation delivery device that employs separate compartments (e.g. blister packs) for each therapeutic agent. Alternatively, the combination may be administered using separate delivery devices, i.e., one delivery device for each therapeutic agent. Additionally, the therapeutic agents can be delivered by different routes of administration, i.e., one by inhalation and the other by oral administration.

Any therapeutic agent compatible with the compounds of the present invention may be used in combination with such compounds. In a particular embodiment, the second therapeutic agent is one that is effectively administered by inhalation. By way of illustration, representative types of therapeutic agents that may be used with the compounds of this invention include, but are not limited to, anti-inflammatory agents, such as steroidal anti-inflammatory agents (including corticosteroids and glucocorticoids), non-steroidal anti-inflammatory agents (NSAIDs), and $PDE_4$ inhibitors; bronchodilators, such as $PDE_3$ inhibitors, adenosine 2b modulators and $\beta_2$ adrenergic receptor agonists; antiinfective agents, such as Gram-positive antibiotics, Gram-negative antibiotics, and antiviral agents; antihistamines; protease inhibitors; afferent blockers, such as $D_2$ agonists and neurokinin modulators; and muscarinic receptor antagonists (antichlolinergic agents). Numerous examples of such therapeutic agents are well known in the art. Suitable doses for the other therapeutic agents administered in combination with a compound of the invention are typically in the range of about 0.05 µg/day to about 500 mg/day.

In a particular embodiment of this invention, a compound of formula I is administered in combination with a steroidal anti-inflammatory agent. Representative examples of steroidal anti-inflammatory agents that can be used in combination with the compounds of this invention include, but are not limited to, beclomethasone dipropionate; budesonide; butixocort propionate; 20R-16α,17α-[butylidenebis(oxy)]-6α,9α-difluoro-11β-hydroxy-17β-(methylthio)androsta-4-en-3-one (RPR-106541); ciclesonide; dexamethasone; 6α,9α-difluoro-17α-[(2-furanylcarbonyl)oxy]-11β-hydroxy-16α-methyl-3-oxoandrosta-1,4-diene-17β-carbothioic acid S-fluoromethyl ester; 6α,9α-difluoro-11β-hydroxy-16α-methyl-17α-[(4-methyl-1,3-thiazole-5-carbonyl)oxy]-3-oxoandrosta-1,4-diene-17β-carbothioic acid S-fluoromethyl ester; 6α,9α-difluoro-11β-hydroxy-16α-methyl-3-oxo-17α-propionyloxyandrosta-1,4-diene-17β-carbothioic acid (S)-(2-oxotetrahydrofuran-3S-yl) ester; flunisolide; fluticasone propionate; methyl prednisolone;

mometasone furoate; prednisolone; prednisone; rofleponide; ST-126; triamcinolone acetonide; and the like, or pharmaceutically acceptable salts thereof. Such steroidal anti-inflammatory agents are commercially available or can be prepared using conventional procedures and reagents. For example, the preparation and use of steroidal anti-inflammatory agents is described in U.S. Pat. No. 6,750,210 B2, issued Jun. 15, 2004; U.S. Pat. No. 6,759,398 B2, issued Jul. 6, 2004; U.S. Pat. No. 6,537,983, issued Mar. 25, 2003; U.S. Patent Application Publication No. US 2002/0019378 A1, published Feb. 14, 2002; and references cited therein.

When employed, the steroidal anti-inflammatory agent is typically administered in an amount that produces a therapeutically beneficial effect when co-administered with a compound of the invention. Typically, the steroidal anti-inflammatory agent will be administered in an amount sufficient to provide from about 0.05 μg to about 500 μg per dose.

The following examples illustrate representative pharmaceutical compositions of the present invention:

EXAMPLE A

Dry Powder Composition

A micronized compound of the invention (100 mg) is blended with milled lactose (25 g) (e.g., lactose in which not greater than about 85% of the particles have a MMD of about 60 μm to about 90 μm and not less than 15% of the particles have a MMD of less then 15 μm). This blended mixture is then loaded into individual blisters of a peelable blister pack in an amount sufficient to provide about 10 μg to about 500 μg of the compound of the invention per dose. The contents of the blisters are administered using a dry powder inhaler.

EXAMPLE B

Dry Powder Composition

A micronized compound of the invention (1 g) is blended with milled lactose (200 g) to form a bulk composition having a weight ratio of compound to milled lactose of 1:200. The blended composition is packed into a dry powder inhalation device capable of delivering between about 10 μg to about 500 μg of the compound of the invention per dose.

EXAMPLE C

Dry Powder Composition

A micronized compound of the invention (100 mg) and a micronized steroidal anti-inflammatory agent (500 mg) are blended with milled lactose (30 g). This blended mixture is then loaded into individual blisters of a peelable blister pack in an amount sufficient to provide about 10 μg to about 500 μg of the compound of the invention per dose. The contents of the blisters are administered using a dry powder inhaler.

EXAMPLE D

Metered-Dose Inhaler Composition

A micronized compound of the invention (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into metered-dose inhaler cartridges containing pressurized 1,1,1,2-tetrafluoroethane in an amount sufficient to provide about 10 μg to about 500 μg of the compound of the invention per dose when administered by the metered dose inhaler.

EXAMPLE E

Nebulizer Composition

A compound of the invention (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1N sodium hydroxide. The solution is administered using a nebulizer device that provides about 10 μg to about 500 μg of the compound of the invention per dose.

EXAMPLE F

Hard Gelatin Capsules

A compound of the invention (50 g), spray-dried lactose (440 g) and magnesium stearate (10 g) are thoroughly blended. The resulting composition is loaded into a hard gelatin capsule (500 mg of composition per capsule) that are administered orally.

EXAMPLE G

Oral Suspension

The following ingredients are thoroughly mixed to form a suspension for oral administration:

| Ingredients | Amount |
| --- | --- |
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| VEEGUM ® K (magnesium aluminum silicate) | 1.0 g |
| Flavoring | 0.035 mL |
| Coloring | 0.5 mg |
| Distilled water | q.s. to 100 mL |

The resulting suspension contains 100 mg of active ingredient per 10 mL of suspension. The suspension is administered orally.

EXAMPLE H

Injectable Composition

A compound of the invention (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Utility

The compounds of this invention possess both $\beta_2$ adrenergic receptor agonist and muscarinic receptor antagonist activity and therefore, such compounds are expected to be useful as therapeutic agents for treating medical conditions mediated by $\beta_2$ adrenergic receptors or muscarinic receptors, i.e., medical conditions that are ameliorated by treatment with a $\beta_2$ adrenergic receptor agonist or a muscarinic receptor antagonist. Such medical conditions are well known to those of ordinary skill in the art as exemplified by the teachings of Eglen et al., *Muscarinic Receptor Subtypes: Pharmacology and Therapeutic Potential*, DN&P 10(8), 462-469 (1997); Emilien et al., *Current Therapeutic Uses and Potential of beta-Adrenoceptor Agonists and Antagonists*, European J. Clinical Pharm., 53(6), 389-404 (1998); and references cited therein. Such medical conditions include, by way of example, pulmonary disorders or diseases associated with reversible airway obstruction, such as chronic obstructive pulmonary disease (e.g., chronic and wheezy bronchitis and emphysema), asthma, pulmonary fibrosis and the like. Other conditions include premature labor, depression, congestive heart failure, skin diseases (e.g., inflammatory, allergic, psoriatic and proliferative skin diseases), conditions where lowering peptic acidity is desirable (e.g., peptic and gastric ulceration) and muscle wasting disease.

Accordingly, in one embodiment, this invention relates to a method for treating a pulmonary disorder, the method comprising administering to a patient in need of treatment a therapeutically effective amount of a compound of formula I. When used to treat a pulmonary disorder, the compounds of this invention will typically be administered by inhalation in multiple doses per day, in a single dose per day or a single dose per week. Generally, the dose for treating a pulmonary disorder will range from about 10 µg/day to about 500 µg/day.

In one of its method aspects, this invention relates to a method of treating chronic obstructive pulmonary disease or asthma, the method comprising administering to a patient a therapeutically effective amount of a compound of formula I. Generally, the dose for treating COPD or asthma will range from about 10 µg/day to about 500 µg/day. The term "COPD" is understood by those of ordinary skill in the art to include a variety of respiratory conditions, including chronic obstructive bronchitis and emphysema, as exemplified by the teachings of Barnes, *Chronic Obstructive Pulmonary Disease*, N. Engl. J. Med., 2000: 343:269-78, and references cited therein.

When administered by inhalation, the compounds of this invention typically have the effect of producing bronchodilation. Accordingly, in another of its method aspects, this invention relates to a method of producing bronchodilation in a mammal, the method comprising administering to a mammal a bronchodilation-producing amount of a compound of formula I. Generally, the dose for producing bronchodilation will range from about 10 µg/day to about 500 µg/day.

When used as a therapeutic agent, the compounds of this invention are optionally administered in combination with another therapeutic agent or agents. In particular, by administering the compounds of this invention with a steroidal anti-inflammatory agent, triple therapy, i.e., $\beta_2$ adrenergic receptor agonist activity, muscarinic receptor antagonist activity and anti-inflammatory activity, can be achieved using only two therapeutic agents. Since pharmaceutical compositions (and combinations) containing two therapeutic agents are typically easier to formulate and/or administer compared to compositions containing three therapeutic agents, such two component compositions provide a significant advantage over compositions containing three therapeutic agents. Accordingly, in a particular embodiment, the pharmaceutical compositions, combinations and methods of this invention further comprise a steroidal anti-inflammatory agent.

Since compounds of this invention possess both $\beta_2$ adrenergic agonist activity and muscarinic receptor antagonist activity, such compounds are also useful as research tools for investigating or studying biological systems or samples having $\beta_2$ adrenergic receptors or muscarinic receptors. Additionally, such compounds are useful in screening assays to discover, for example, new compounds having both $\beta_2$ adrenergic agonist activity and muscarinic receptor antagonist activity. Such biological systems or samples may comprise $\beta_2$ adrenergic receptors and/or muscarinic receptors. Any suitable biological system or sample having $\beta_2$ adrenergic and/or muscarinic receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.), and the like.

When used as a research tool, a biological system or sample comprising a $\beta_2$ adrenergic receptor and/or a muscarinic receptor is typically contacted with a $\beta_2$ adrenergic receptor-agonizing or muscarinic receptor-antagonizing amount of a compound of this invention. The effects on the biological system or sample caused by the compound are then determined or measured using conventional procedures and equipment, such as by measuring binding in a radioligand binding assays or ligand-mediated changes in a functional assay or by determining the amount of bronchoprotection provided by the compound in a bronchoprotection assay in a mammal. Representative ligand-mediated changes in a functional assay include ligand-mediated changes in intracellular cyclic adenosine monophosphate (cAMP); ligand-mediated changes in activity of the enzyme adenylyl cyclase (which synthesizes cAMP); ligand-mediated changes in incorporation of guanosine 5'-O-(thio)triphosphate ([$^{35}$S]GTP S) into isolated membranes via receptor catalyzed exchange of [$^{35}$S] GTP S for GDP; ligand-mediated changes in free intracellular calcium ions (measured, for example, with a fluorescence-linked imaging plate reader or FLIPR® from Molecular Devices, Inc.); and the like. Compounds of this invention are expected to agonize or cause activation of a $\beta_2$ adrenergic receptor and antagonize or decrease the activation of muscarinic receptors in the functional assays listed herein or in assays of a similar nature. The compounds of this invention will typically be used in these studies at a concentration ranging from about 0.1 nanomolar to about 100 nanomolar.

Additionally, the compounds of this invention can be used as research tools for evaluating other chemical compounds. In this aspect of the invention, a compound of formula I is used as a standard in an assay to allow comparison of the results obtained with a test compound and the compound of formula I. For example, $\beta_2$ adrenergic receptor and/or muscarinic receptor binding data (as determined, for example, by in vitro radioligand displacement assays) for a test compound or a group of test compounds is compared to the $\beta_2$ adrenergic receptor and/or muscarinic receptor binding data for a compound of formula I to identify those test compounds that have desirable binding, i.e. test compounds having binding about equal or superior to a compound of formula I, if any. Alternatively, for example, bronchoprotective effects can be determined for test compounds and a compound of formula I in a bronchoprotection assay in a mammal and this data compared to identify test compounds providing about equal or superior bronchoprotective effects. This aspect of the invention includes, as separate embodiments, both (i) the generation of comparison data (using the appropriate assays) and (ii) the analysis of the test data to identify test compounds of interest.

The properties and utility of the compounds of this invention can be demonstrated using various in vitro and in vivo assays well known to those of ordinary skill in the art. For example, representative assays are described in further detail in the following Examples.

EXAMPLES

The following Preparations and Examples are provided to illustrate specific embodiments and aspects of this invention. The illustration of specific embodiments and aspects, however, is not intended to limit the scope of this invention in any way unless specifically indicated.

All reagents, starting materials and solvents used in the following examples were purchased from commercial suppliers (such as Aldrich, Fluka, Sigma and the like) and were used without further purification unless otherwise indicated.

In the following examples, HPLC analysis was typically conducted using an Agilent (Palo Alto, Calif.) Series 1100 instrument with Zorbax Bonus RP 2.1×50 mm columns, supplied by Agilent, (a C14 column), having a 3.5 micron particle size. Detection was by UV absorbance at 214 nm. Mobile phase "A" was 2% acetonitrile, 97.9% water, and 0.1% trifluoroacetic acid (v/v/v); and mobile phase "B" was 89.9% acetonitrile, 10% water, and 0.1% trifluoroacetic acid (v/v/v). HPLC (10-70) data were obtained with a flow rate of 0.5 mL/minute of 10% to 70% mobile phase B gradient over a 6-minute period; HPLC (5-35) data were obtained with a flow rate of 0.5 mL/minute of 5% to 35% mobile phase B gradient over a 5-minute period; and HPLC (10-90) data were obtained with a flow rate of 0.5 mL/minute of 10% to 90% mobile phase B gradient over a 5-minute period.

Liquid chromatography mass spectrometry (LCMS) data typically were obtained with an Applied Biosystems (Foster City, Calif.) Model API-150EX instrument. LCMS 10-90 data were obtained with a 10% to 90% mobile phase B gradient over a 5-minute period.

Small-scale purifications were typically conducted using an API 150EX Prep Workstation system from Applied Biosystems. The mobile phase "A" was water containing 0.05% trifluoroacetic acid (v/v); and mobile phase "B" was acetonitrile containing 0.05% trifluoroacetic acid (v/v). For small samples (about 3 to 50 mg recovered sample size), the following conditions were typically used: 20 mL/min flow rate; 15 min gradients and a 20 mm×50 mm Prism RP column with 5 micron particles (Thermo Hypersil-Keystone, Bellefonte, Pa.). For larger samples (i.e., greater than about 100 mg crude sample), the following conditions were typically used: 60 mL/min flow rate; 30 min gradients and a 41.4 mm×250 mm Microsorb BDS column with 10 micron particles (Varian, Palo Alto, Calif.).

For $^1$H NMR data, the following abbreviations are used: s=singlet, d=doublet, t=triplet, q=quartet, m=multiplet, br=broad, nd=not determined.

Example 1

Biphenyl-2-ylcarbamic Acid Piperidin-4-yl Ester

Biphenyl-2-isocyanate (97.5 g, 521 mmol) and 4-hydroxy-1-benzylpiperidine (105 g, 549 mmol) (both commercially available from Aldrich, Milwaukee, Wis.) were heated together at 70° C. for 12 h, during which time the formation of biphenyl-2-ylcarbamic acid 1-benzylpiperidin-4-yl ester was monitored by LCMS. The reaction mixture was then cooled to 50° C. and ethanol (1 L) was added, and then 6M hydrochloric acid (191 mL) was added slowly. The reaction mixture was then cooled to ambient temperature and ammonium formate (98.5 g, 1.56 mol) was added and nitrogen gas was bubbled through the solution vigorously for 20 min. Palladium (10 wt. % (dry basis) on activated carbon) (20 g) was then added. The reaction mixture was heated at 40° C. for 12 h and then filtered through a pad of Celite. The solvent was then removed under reduced pressure and 1M hydrochloric acid (40 mL) was added to the crude residue. Sodium hydroxide (10N) was then added to adjust the pH to 12. The aqueous layer was extracted with ethyl acetate (2×150 mL) and dried (magnesium sulfate), and then the solvent was removed under reduced pressure to give biphenyl-2-ylcarbamic acid piperidin-4-yl ester (155 g, 100%). HPLC (10-70) $R_t$=2.52; MS m/z: [M+H$^+$] calc'd for $C_{18}H_{20}N_2O_2$ 297.15; found 297.3.

Example 2

3-[4-(Biphenyl-2-ylcarbamoyloxy)piperidin-1-yl] propionic Acid

To a solution of biphenyl-2-ylcarbamic acid piperidin-4-yl ester (50 g, 67.6 mmol) in dichloromethane (500 mL) was added acrylic acid (15.05 mL, 100 mmol). The resulting mixture was heated at 50° C. under reflux for 18 hours and then the solvent was removed. Methanol (600 mL) was added and this mixture was heated at 75° C. for 2 hours and cooled to room temperature to form a thick slurry. The solid was collected by filtration, washed with methanol (50 mL) and air dried to afford 3-[4-(biphenyl-2-ylcarbamoyloxy)piperidin-1-yl]propionic acid (61 g, 96% purity) as white powder.

Example 3

N-{5-[(R)-2-Amino-1-(tert-butyldimethylsilanyloxy) ethyl]-2-hydroxyphenyl}-formamide Acetic Acid Salt Step A—N-{5-[(R)-2-Benzylamino-1-(tert-butyldimethylsilanyloxy)ethyl]-2-benzyloxyphenyl}formamide To a 500 mL three-necked round-bottomed flask was added N-{2-benzyloxy-5-[(R)-2-bromo-1-(tert-butyldimethylsilanyloxy)ethyl]phenyl}formamide (100 g, 215 mmol) and N-methyl-2-pyrrolidone (300 mL). Benzylamine (69.4 mL, 648 mol) was added and the reaction mixture was flushed with nitrogen. The reaction mixture was then heated to 90° C. and stirred for about 8 hours. The reaction mixture was then cooled to room temperature and water (1.5 L) and ethyl acetate (1.5 L) were added. The layers were separated and the organic layer was washed with water (500 mL), a 1:1 mixture of water and saturated brine (500 mL total), and then again with water (500 mL). The organic layer was then dried over anhydrous magnesium sulfate, filtered and concentrated under reduced pressure to provide crude N-{5-[(R)-2-benzylamino-1-(tert-butyldimethylsilanyloxy)ethyl]-2-benzyloxyphenyl}formamide (100 g, 90% yield, 75-80% purity) as an orange-brown thick oil.

Step B—N-{5-[(R)-2-Amino-1-(tert-butyldimethylsilanyloxy)ethyl]-2-hydroxyphenyl}-formamide Acetic Acid Salt Crude N-{5-[(R)-2-benzylamino-1-(tert-butyldimethylsilanyloxy)ethyl]-2-benzyloxyphenyl}formamide (100 g, 194 mmol) was dissolved in methanol (1 L) and acetic acid (25 mL, 291 mmol). The resulting mixture was purged with dry nitrogen and then palladium hydroxide on carbon (20 g, 20 wt. %, about 50% water) was added. Hydrogen was bubbled through the reaction mixture with stirring at room temperature for about 10 hours. The mixture was then purged with dry nitrogen and the mixture was filtered through Celite. The filtrate was concentrated on a rotary evaporator and ethyl acetate (600 mL) was added to the residue. This mixture was stirred for about 2 hours at which time a thick yellow slurry had developed. The slurry was filtered and the precipitate was air dried to provide N-{5-[(R)-2-amino-1-(tert-butyldimethylsilanyloxy)ethyl]-2-hydroxyphenyl}formamide acetic acid salt (48 g, 98% purity) as a yellow-white solid. LCMS (10-70) $R_t$=3.62; [M+H$^+$] found 311.3.

Example 4

Biphenyl-2-ylcarbamic Acid 1-[2-(4-{[(R)-2-(3-Formylamino-4-hydroxyphenyl)-2-hydroxyethylamino]methyl}-2,5-dimethylphenylcarbamoyl)ethyl]piperidin-4-yl Ester Step A—Methyl 2,5-Dimethyl-4-nitrobenzoate To a stirred solution of 2,5-dimethyl-4-nitrobenzoic acid (480 mg, 2.4 mmol) in dry methanol (8.2 mL) at 0° C. under dry nitrogen was added thionyl chloride (0.538 mL, 7.38 mmol). The resulting mixture as allowed to warm to room temperature and stirred for about 7 hours. Additional thionyl chloride (0.300 mL) was added and stirring was continued at room temperature overnight. The solvent was removed under reduced pressure and the residue was dissolved in ethyl acetate. This solution was washed with saturated aqueous sodium bicarbonate, dried over anhydrous sodium sulfate and concentrated under reduced pressure to provide methyl 2,5-dimethyl-4-nitrobenzoate (578 mg) as a pale yellow solid. HPLC (10-70) $R_t$=4.61; $^1$H NMR (300 MHz, CDCl$_3$) δ 2.57 (s, 3H), 2.61 (s, 3H), 3.94 (s, 3H), 7.82 (s, 1H), 7.87 (s, 1H).

Step B—Methyl 4-Amino-2,5-dimethylbenzoate

To a stirred solution of methyl 2,5-dimethyl-4-nitrobenzoate (523 mg, 2.5 mmol) in a 9:1 mixture of methanol and water (25 mL total) at 0° C. was added ammonium chloride (401 mg, 7.5 mmol). Zinc (1.63 g, 25 mmol) was added portionwise and the resulting mixture was stirred at room temperature overnight. The reaction mixture was then filtered through Celite and the Celite pad was washed with methanol. The filtrate was concentrated under reduced pressure and the resulting residue was dissolved in ethyl acetate. This solution was washed with saturated aqueous sodium bicarbonate, dried over anhydrous sodium sulfate and concentrated under reduced pressure to provide methyl 4-amino-2,5-dimethylbenzoate (450 mg) as a yellow oil. $^1$H NMR (300 MHz, CDCl$_3$) δ 2.14 (s, 3H), 2.53 (s, 3H), 3.83 (s, 3H), 3.85 (br s, 2H), 6.48 (s, 1H), 7.72 (s, 1H).

Step C—Methyl 4-{3-[4-(Biphenyl-2-ylcarbamoyloxy)piperidin-1-yl]propionylamino}-2,5-dimethylbenzoate To a stirred solution of 3-[4-(biphenyl-2-ylcarbamoyloxy)piperidin-1-yl]propionic acid (670 mg, 1.82 mmol) and methyl 4-amino-2,5-dimethylbenzoate (390 mg, 2.18 mmol) in dichloromethane (3.6 mL) and diisopropylethylamine (0.413 mL) was added O-(7-azabenzotriazol-1-yl)-1,1,3,3-tetramethyluronium hexafluorophosphate (HATU) (829 mg, 2.18 mmol). The resulting mixture was stirred at room temperature overnight. The mixture was then washed with saturated aqueous sodium bicarbonate, dried over anhydrous sodium sulfate, filtered and concentrated under reduced pressure. The residue was purified by silica gel chromatography eluting with dichloromethane containing from 3% to 5% methanol to provide methyl 4-{3-[4-(biphenyl-2-ylcarbamoyloxy)piperidin-1-yl]propionylamino}-2,5-dimethylbenzoate (568 mg, 59% yield). LCMS (10-70) $R_t$=4.55; [M+H$^+$] found 530.4.

Step D—Biphenyl-2-ylcarbamic Acid 1-[2-(4-Hydroxymethyl-2,5-dimethylphenylcarbamoyl)ethyl]piperidin-4-yl Ester To a stirred solution of 1M lithium aluminum hydride in THF (1.52 mL, 1.52 mmol) at 0° C. was added methyl 4-{3-[4-(biphenyl-2-ylcarbamoyloxy)piperidin-1-yl]propionylamino}-2,5-dimethylbenzoate (400 mg, 0.76 mmol). The resulting mixture was stirred at 0° C. for 30 minutes and then a 1:1 mixture of 1M aqueous sodium hydroxide (5 mL) and water (5 mL) was added and stirring was continued for 2 hours. Dichloromethane was added and the organic layer was separated, dried over sodium sulfate and the solvent removed under reduced pressure. The residue was purified by silica gel chromatography eluting with dichloromethane containing 5% methanol to provide biphenyl-2-ylcarbamic acid 1-[2-(4-hydroxymethyl-2,5-dimethylphenylcarbamoyl)-ethyl]piperidin-4-yl ester. LCMS (10-70) $R_t$=3.94; [M+H$^+$] found 502.5.

Step E—Biphenyl-2-ylcarbamic Acid 1-[2-(4-Formyl-2,5-dimethylphenylcarbamoyl)ethyl]piperidin-4-yl Ester To a solution of biphenyl-2-ylcarbamic acid 1-[2-(4-hydroxymethyl-2,5-dimethylphenylcarbamoyl)ethyl]piperidin-4-yl ester (151 mg, 0.3 mmol) in dichloromethane (3 mL) at 0° C. was added dimethyl sulfoxide (128 μL, 1.8 mmol) and diisopropylethylamine (157 μL, 0.9 mmol). After 15 minutes, sulfur trioxide pyridine complex (143 mg, 0.9 mmol) was added and stirring at 0° C. was continued for 1 hour. Water was added to quench the reaction and the layers were separated. The organic layer was dried over anhydrous sodium sulfate, filtered and the solvent removed under reduced pressure to give biphenyl-2-ylcarbamic acid 1-[2-(4-formyl-2,5-dimethylphenylcarbamoyl)ethyl]piperidin-4-yl ester (150 mg, 100% yield), which was used without further purification. [M+H$^+$] found 500.4.

Step F—Biphenyl-2-ylcarbamic Acid 1-[2-(4-{[(R)-2-(tert-Butyldimethylsilanyloxy)-2-(3-formylamino-4-hydroxyphenyl)ethylamino]methyl}-2,5-dimethylphenylcarbamoyl)ethyl]piperidin-4-yl Ester A solution of biphenyl-2-ylcarbamic acid 1-[2-(4-formyl-2,5-dimethylphenylcarbamoyl)ethyl]piperidin-4-yl ester (150 mg, 0.30 mmol) and N-{5-[(R)-2-amino-1-(tert-butyldimethylsilanyloxy)ethyl]-2-hydroxyphenyl}formamide (112 mg, 0.36 mmol) in a 1:1 mixture of dichloromethane and methanol (3.0 mL total) was stirred at room temperature for 30 minutes. Sodium triacetoxyborohydride (191 mg, 0.9 mmol) was added and the resulting mixture was stirred at room temperature overnight. Acetic acid was added to quench the reaction and the mixture was concentrated under reduced pressure to give biphenyl-2-ylcarbamic acid 1-[2-(4-{[(R)-2-(tert-butyldimethylsilanyloxy)-2-(3-formylamino-4-hydroxyphenyl)ethylamino]methyl}-2,5-dimethylphenylcarbamoyl)-ethyl]piperidin-4-yl ester, which was used without further purification. LCMS (10-70) $R_f$=4.55; [M+H$^+$] found 794.6.

Step G—Biphenyl-2-ylcarbamic Acid 1-[2-(4-{[(R)-2-(3-Formylamino-4-hydroxyphenyl)-2-hydroxy-ethylamino]methyl}-2,5-dimethylphenylcarbamoyl)ethyl]piperidin-4-yl Ester To a suspension of biphenyl-2-ylcarbamic acid 1-[2-(4-{[(R)-2-(tert-butyldimethylsilanyloxy)-2-(3-formylamino-4-hydroxyphenyl)ethylamino]methyl}-2,5-dimethylphenyl-carbamoyl)-ethyl]piperidin-4-yl ester (238 mg, 0.30 mmol) in dichloromethane (3.0 mL) was added triethylamine trihydrofluoride (147 μL, 0.90 mmol). This mixture was stirred at room temperature overnight and then the mixture was concentrated under reduced pressure. The residue was purified by prep-RP-HPLC (gradient: 2 to 50% acetonitrile in water with 0.05% TFA). The appropriate fractions were collected and combined and lyophilized to give biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester as the ditrifluoroacetate salt (50 mg, 97% purity). LPLC (2-90) $R_f$=2.76; [M+H$^+$] found 680.8.

Example 5

Biphenyl-2-ylcarbamic Acid 1-[2-(4-{[(R)-2-(3-Formylamino-4-hydroxyphenyl)-2-hydroxyethy-lamino]methyl}-2,5-dimethylphenylcarbamoyl)ethyl]piperidin-4-yl Ester Step A—Dibenzyl-(4-iodo-2,5-dimethylphenyl)amine To a 2-liter round-bottomed flask equipped with an overhead stirrer, temperature control and an addition funnel was added 4-iodo-2,5-dimethylaniline (100.0 g, 0.405 mol) (from Spectra Group Limited, Inc., Millbury, Ohio). Ethanol (1 L) and solid potassium carbonate (160 g, 1.159 mol) were added and then neat benzyl bromide (140 mL, 1.179 mol) was added in one portion. The resulting mixture was stirred at 30° C. for about 18 hours at which time HPLC shows greater than 98% conversion. The mixture was then cooled to room temperature and hexanes (1 L) were added. This mixture was stirred for 15 minutes and then filtered through a paper filter to removed solids and the filter cake was washed with hexanes (200 mL). Using a rotoevaporator, the volume of the filtrate was reduced to about 500 mL and concentrated hydrochloric acid (30 mL) was added. The remaining solvent was then removed using a rotoevaporator. To the resulting residue was added hexanes (500 mL) and this mixture was stirred for about 30 minutes as which time a free-flowing slurry had formed. The slurry was filtered and the filter cake was washed with hexanes (200 mL) and dried to provide dibenzyl-(4-iodo-2,5-dimethylphenyl)amine hydrochloride (115 g, 62% yield, 97.5% purity) as a greenish colored solid.

The dibenzyl-(4-iodo-2,5-dimethylphenyl)amine hydrochloride was transferred to a 3 L flask and toluene (1 L) and 1 M aqueous sodium hydroxide (1 L) were added. The resulting mixture was stirred for 1 hour and then the layers were separated. The organic layer was washed with dilute brine (500 mL) and the solvent was removed by rotoevaporation to provide dibenzyl-(4-iodo-2,5-dimethylphenyl)amine (80 g) as a semi-solid thick oil. (Alternatively, dichloromethane can be used in place of toluene in this step). $^1$H NMR (300 MHz, DMSO-d$_6$) δ 2.05 (s, 3H), 2.19 (s, 3H), 3.90 (s, 4H), 6.91 (s, 1H), 7.05-7.20 (m, 10H), 7.42 (s, 1H); MS [M+H$^+$] found 428.

Step B—4-Dibenzylamino-2,5-dimethylbenzaldehyde Hydrochloride

To a 1-liter 3-necked round-bottomed flask equipped with an overhead stirrer, temperature control and an addition funnel was added dibenzyl-(4-iodo-2,5-dimethylphenyl)amine (15 g, 35 mmol). Toluene (300 mL) was added and the resulting mixture was stirred for about 15 minutes. The reaction flask was purged with dry nitrogen and cooled to about −20° C. and 1.6 M n-butyllithium in hexanes (33 mL, 53 mmol) was added dropwise via the addition funnel. During the addition, the internal temperature of the reaction mixture was maintained below −10° C. When the addition was complete, the resulting mixture was stirred at about −15° C. for 15 minutes. N,N-Dimethylformamide (10 mL, 129 mmol) was then added dropwise while maintaining the internal reaction temperature below 0° C. The resulting mixture was then stirred at −20° C. to 0° C. for about 1 hour. Aqueous 1 M hydrochloric acid (200 mL) was then added over a 5 minute period and the resulting mixture was stirred for 15 minutes. The layers were then separated and the organic layer was washed with dilute brine (100 mL). The organic layer was then dried over anhydrous sodium sulfate, filtered and the solvent removed under reduced pressure to provide 4-dibenzylamino-2,5-dimethylbenzaldehyde hydrochloride (11.5 g, 90% yield, 95% purity) as thick oil that solidified upon standing. The product contained about 3 to 5% of the des-iodo by-product. $^1$H NMR (300 MHz, CDCl$_3$) δ 2.42 (s, 3H), 2.50 (s, 3H), 4.25 (s, 4H), 6.82 (s, 1H), 7.10-7.30 (m, 10H), 7.62 (s, 1H), 10.15 (s, 1H); MS [M+H$^+$] found 330.3.

Step C—4-[1,3]Dioxolan-2-yl-2,5-dimethylphenylamine

To a 500 mL round-bottomed flask was added 4-dibenzylamino-2,5-dimethylbenzaldehyde hydrochloride (11.5 g, 31.4 mmol) and toluene (150 mL) and the resulting mixture was stirred until the salt completely dissolved. The reaction flask was then purged with dry nitrogen for 5 minutes. Ethylene glycol (5.25 mL, 94.2 mmol) and p-toluenesulfonic acid (760 mg, 6.2 mmol) were added and the resulting mixture was heated at 60° C. to 80° C. for about 20 hours. The solvent was then removed slowly (over about 40 minutes) at 40° C. on a rotary evaporator. Toluene (100 mL) was added to the residue and the solvent was again removed slowly at 40° C. on a rotary evaporator. This process was repeated using another aliquot of toluene (100 mL) and the mixture was evaporated to dryness. Ethyl acetate (150 mL) and saturated aqueous sodium bicarbonate (100 mL) were added to the residue and the layers were separated. The organic layer was washed with brine (50 mL) and then dried over anhydrous sodium sulfate, filtered and concentrated under reduced pressure to provide crude dibenzyl-(4-[1,3]dioxolan-2-yl-2,5-dimethyl-phenyl)amine (11.4 g).

The crude dibenzyl-(4-[1,3]dioxolan-2-yl-2,5-dimethyl-phenyl)amine was dissolved in a 2:1 mixture of ethanol and water (150 mL total) and the resulting mixture was purged with dry nitrogen for 5 minutes. Palladium on carbon (2.3 g, 10 wt. % containing about 50% water) and solid sodium bicarbonate (1.0 g) were added and the resulting mixture was hydrogenated at about 1 atm of hydrogen at 25° C. to 30° C. for about 8 hours. The mixture was then filtered through Celite and the filtrate was concentrated on a rotary evaporator to provide crude 4-[1,3]dioxolan-2-yl-2,5-dimethylphenylamine (5.6 g, 92% yield) as a thick oil. $^1$H NMR (300 MHz, DMSO-$d_6$) δ 2.05 (s, 3H), 2.22 (s, 3H), 3.7-3.9 (m, 4H), 3.95 (s, 4H), 5.59 (s, 1H), 6.72 (s, 1H), 7.0-7.25 (m, 11H).

Step D-N-(4-[1,3]Dioxolan-2-yl-2,5-dimethylphenyl)acrylamide

To a 500 mL round-bottom flask was added crude 4-[1,3]dioxolan-2-yl-2,5-dimethylphenylamine (5.6 g, 29 mmol), dichloromethane (100 mL) and diisopropylethylamine (7.6 mL, 43.5 mmol). The resulting mixture was stirred at room temperature until the ingredients dissolved and then the mixture was cooled to 0° C. Acryloyl chloride (2.35 mL, 29 mmol) was then added dropwise over a 5 minute period. The reaction mixture was stirred at 0° C. to 5° C. for 1 hour and then water (50 mL) was added and stirring was continued for about 30 minutes at which time fine solids had formed. The mixture was filtered to collect the solids. The layers of the filtrate were then separated and the organic layer was concentrated under reduced pressure to dryness. Dichloromethane (50 mL) was added to the residue and this mixture was stirred until a free-flowing slurry developed. The slurry was filtered (using the same funnel used to collect the fine solids above) and the filter cake was washed with dichloromethane (10 mL) and dried to provide N-(4-[1,3]dioxolan-2-yl-2,5-dimethylphenyl)acrylamide (3.1 g, 97% purity) as a white to off-white solid.

The filtrate from above was then evaporated to dryness and methanol (10 mL) was added to the residue. This mixture was stirred for 15 minutes and then the precipitate was collected by filtration, washed with methanol (5 mL) and dried to give a second crop of N-(4-[1,3]dioxolan-2-yl-2,5-dimethylphenyl)acrylamide (0.8 g, 95% purity). $^1$H NMR (300 MHz, CD$_3$OD) δ 2.10 (s, 3H), 2.23 (s, 3H), 3.85-4.10 (m, 4H), 5.60-6.40 (m, 3H), 5.59 (s, 1H), 7.18 (s, 1H), 7.23 (s, 1H).

Step E—Biphenyl-2-ylcarbamic Acid 1-[2-(4-Formyl-2,5-dimethylphenylcarbamoyl)ethyl]piperidin-4-yl Ester Hydrochloride To a 50 mL round-bottom flask was added biphenyl-2-ylcarbamic acid piperidin-4-yl ester (1.2 g, 4.04 mmol) and N-(4-[1,3]dioxolan-2-yl-2,5-dimethylphenyl)acrylamide (1.0 g, 4.04 mmol). Ethanol (10 mL) and dichloromethane (10 mL) were added to form a slurry. The reaction mixture was heated at 45° C. to 50° C. for about 18 hours and then cooled to room temperature. Aqueous 1M hydrochloric acid (10 mL) was added and the resulting mixture was stirred vigorously for about 3 hours. Dichloromethane (10 mL) was added and the resulting mixture was stirred for about 5 minutes. The layers were then separated and the organic layer was dried over anhydrous sodium sulfate, filtered and concentrated on a rotary evaporator to provide crude biphenyl-2-ylcarbamic acid 1-[2-(4-formyl-2,5-dimethylphenylcarbamoyl)ethyl]piperidin-4-yl ester hydrochloride (1.9 g). $^1$H NMR (300 MHz, DMSO-$d_6$) δ 1.2-1.4 (m, 2H), 1.58-1.75 (m, 2H), 2.0-2.17 (m, 2H), 2.19 (s, 3H), 2.38 (s, 3H), 2.41-2.50 (m, 4H), 2.5-2.75 (m, 2H), 4.31-4.42 (m, 1H), 7.10-7.35 (m, 9H), 7.55 (s, 1H), 7.75 (s, 1H), 8.59 (s, 1H), 9.82 (s, 1H), 9.98 (s, 1H); MS [M+H$^+$] found 500.2.

Step F—Biphenyl-2-ylcarbamic Acid 1-[2-(4-{[(R)-2-(tert-Butyldimethylsilanyloxy)-2-(3-formylamino-4-hydroxyphenyl)ethylamino]methyl}-2,5-dimethylphenyl-carbamoyl)ethyl]piperidin-4-yl Ester To a 2 L three-necked round-bottom flask was added biphenyl-2-ylcarbamic acid 1-[2-(4-formyl-2,5-dimethylphenylcarbamoyl)ethyl]piperidin-4-yl ester hydrochloride (38 g, 70 mmol) and N-{5-[(R)-2-amino-1-(tert-butyldimethylsilanyloxy)ethyl]-2-hydroxyphenyl}formamide acetic acid salt (33.6 g, 91 mmol). Dichloromethane (500 mL) and methanol (500 mL) were added and the resulting mixture was stirred at room temperature under dry nitrogen for about 3 hours. The reaction mixture was then cooled to 0° C. to 5° C. and solid sodium triacetoxyborohydride (44.5 g, 381 mmol) was added in portions over a 10 minute period. The reaction mixture was slowly warmed from 0° C. to room temperature over a period of about 2 hours and then cooled to 0° C. Saturated aqueous sodium bicarbonate (500 mL) and dichloromethane (500 mL) were added. This mixture was stirred thoroughly and then the layers were separated. The organic layer was washed with brine (500 mL), dried over anhydrous sodium sulfate, filtered and concentrated under reduced pressure to give crude biphenyl-2-ylcarbamic acid 1-[2-(4-{[(R)-2-(tert-butyldimethylsilanyloxy)-2-(3-formylamino-4-hydroxyphenyl)ethylamino]methyl}-2,5-dimethylphenylcarbamoyl)-ethyl]piperidin-4-yl ester (55 g, 86% purity) as a yellow solid.

The crude product (30 g) was dissolved in dichloromethane containing 2% methanol (150 mL total) and loaded onto a silica gel column (300 g) that had been packed and equilibrated with dichloromethane containing 2% methanol and 0.5% ammonium hydroxide. The product was eluted from the column using dichloromethane containing 2% methanol and 0.5% ammonium hydroxide (1 L); dichloromethane containing 4% methanol and 0.5% ammonium hydroxide (1 L) and dichloromethane containing 5% methanol and 0.5% ammonium hydroxide (about 3 L). Fractions (200 mL) were collected and those fractions having a purity greater than 90% were combined and concentrated under reduced pressure to provide biphenyl-2-ylcarbamic acid 1-[2-(4-{[(R)-2-(tert-butyldimethylsilanyloxy)-2-(3-formylamino-4-hydroxyphenyl)ethylamino]methyl}-2,5-dimethylphenylcarbamoyl)-ethyl]piperidin-4-yl ester (21.6 g, 96.5% purity) as a yellowish solid. MS [M+H$^+$] found 794.6.

Step G—Biphenyl-2-ylcarbamic Acid 1-[2-(4-{[(R)-2-(3-Formylamino-4-hydroxyphenyl)-2-hydroxyethylamino]methyl}-2,5-dimethylphenyl-carbamoyl)ethyl]piperidin-4-yl Ester Hydrofluoride Salt To a 1 L round-bottom flask was added biphenyl-2-ylcarbamic acid 1-[2-(4-{[(R)-2-(tert-butyldimethylsilanyloxy)-2-(3-formylamino-4-hydroxyphenyl)ethylamino]methyl}-2,5-dimethylphenylcarbamoyl)ethyl]piperidin-4-yl ester (21.5 g, 27.1 mmol) and dichloromethane (200 mL). The resulting mixture was stirred at room temperature until the ingredients dissolved and then triethylamine trihydrofluoride (8.85 mL, 54.2 mmol) was added and the resulting mixture was stirred at 25° C. for about 48 hours. The solvent was removed on a rotary evaporator to provide a thick paste. Dichloromethane (100 mL) and ethyl acetate (200 mL) were added to the paste and the resulting mixture was stirred for 30 minutes. The resulting slurry was slowly filtered under dry nitrogen and the filter cake was washed with a 1:2 mixture of dichloromethane and ethyl acetate (100 mL total), dried under nitrogen for 2 hours and then dried under vacuum overnight to provide biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester as a hydrofluoride salt (25 g, 96.9% purity) which was a hard clay-like solid. MS [M+H$^+$] found 680.8.

Step H—Biphenyl-2-ylcarbamic Acid 1-[2-(4-{[(R)-2-(3-Formylamino-4-hydroxyphenyl)-2-hydroxyethylamino]methyl}-2,5-dimethylphenylcarbamoyl)ethyl]piperidin-4-yl Ester Biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester hydrofluoride salt (25 g) was purified on a 6-inch reverse-phase column (Microsorb solid phase) in three equal batches using a 10% to 50% mixture of acetonitrile in water containing 1% trifluoroacetic acid as the mobile phase. Fractions with greater than 99% purity were combined and then diluted with one volume of water. The resulting mixture was cooled to 0° C. and solid sodium bicarbonate was added until the pH of the mixture was about 7.5 to 8.0. Within about 5 minutes, a white slurry developed. The slurry was stirred for 30 minutes and then filtered. The filter cake was washed with water (500 mL), air dried for about 4 hours and then dried in vacuum overnight to provide biphenyl-2-ylcarbamic acid 1-[2-(4-{[(R)-2-(3-formylamino-4-hydroxyphenyl)-2-hydroxyethylamino]methyl}-2,5-dimethylphenyl-carbamoyl)ethyl]piperidin-4-yl ester (12 g, 99+% purity), as a semi-crystalline free base.

Example 6

Biphenyl-2-ylcarbamic Acid 1-[2-(4-{[(R)-2-(3-Formylamino-4-hydroxyphenyl)-2-hydroxyethylamino]methyl}-2,5-dimethylphenylcarbamoyl)ethyl]piperidin-4-yl Ester

Step A—Biphenyl-2-ylcarbamic Acid 1-[2-(4-[1,3]-Dioxolan-2-yl-2,5-dimethylphenylcarbamoyl)ethyl]piperidin-4-yl Ester To a 500 mL round-bottom flask was added biphenyl-2-ylcarbamic acid piperidin-4-yl ester (17.0 g, 58 mmol) and N-(4-[1,3]dioxolan-2-yl-2,5-dimethylphenyl)acrylamide (13.1 g, 52.9 mmol). Ethanol (150 mL) and dichloromethane (150 mL) were added to form a slurry. The reaction mixture was heated at 50° C. to 55° C. for about 24 hours and then cooled to room temperature. Most of the solvent was removed on a rotary evaporator, resulting in a thick slurry. Ethanol (reagent grade) was added to form a total volume of about 200 mL and the resulting mixture was heated to 80° C. and then cooled slowly to room temperature. The resulting thick white slurry was filtered, washed with ethanol (20 mL) and dried in vacuum to provide biphenyl-2-ylcarbamic acid 1-[2-(4-[1,3]dioxolan-2-yl-2,5-dimethylphenylcarbamoyl)ethyl]piperidin-4-yl ester (23.8 g, about 98% purity) as a white solid.

Step B—Biphenyl-2-ylcarbamic Acid 1-[2-(4-Formyl-2,5-dimethylphenyl-carbamoyl)ethyl]piperidin-4-yl Ester To a 500 mL round-bottom flask was added biphenyl-2-ylcarbamic acid 1-[2-(4-[1,3]dioxolan-2-yl-2,5-dimethylphenylcarbamoyl)ethyl]piperidin-4-yl ester (15 g, 27.6 mmol) and acetonitrile (150 mL) to form a slurry. Aqueous 2 M hydrochloric acid (75 mL) was added and the resulting mixture was stirred at 30° C. for 1 hour. The mixture was then cooled to room temperature and ethyl acetate (150 mL) was added. Aqueous 2 M sodium hydroxide (75 mL) was added, the pH was checked and then additional 2 M sodium hydroxide was added until the pH of the solution was in the range of 9 to 10. The layers were separated and the organic layer was washed with diluted brine (75 mL; 1:1 brine/water), dried over anhydrous sodium sulfate and the solvent removed on a rotary evaporator to give biphenyl-2-ylcarbamic acid 1-[2-(4-formyl-2,5-dimethylphenyl-carbamoyl)ethyl]piperidin-4-yl ester (12.5 g, about 98% purity). If desired, the purity of this intermediate can be increased by forming a slurry with ethanol (3 volumes of ethanol), heating the slurry to 80° C., and then cooling slowly to room temperature and isolating by filtration.

Step C—Biphenyl-2-ylcarbamic Acid 1-[2-(4-{[(R)-2-(tert-Butyldimethylsilanyloxy)-2-(3-formylamino-4-hydroxyphenyl)ethylimino]methyl}-2,5-dimethylphenylcarbamoyl)ethyl]piperidin-4-yl Ester To a 250 mL round-bottom flask was added biphenyl-2-ylcarbamic acid 1-[2-(4-formyl-2,5-dimethylphenylcarbamoyl)ethyl]piperidin-4-yl ester (7.1 g, 14.2 mmol) and N-{5-[(R)-2-amino-1-(tert-butyldimethylsilanyloxy)ethyl]-2-hydroxyphenyl}formamide acetic acid salt (5.8 g, 15.6 mmol). Methanol (100 mL) was added to form a slurry and this mixture was stirred at 45° C. to 50° C. under nitrogen for 1 hour. The mixture was then cooled to room temperature and toluene (50 mL) was added and the solvent was removed on a rotary evaporator at temperature ranging from 35° C. to 45° C. Toluene (50 mL) was added to the residue and the solvent was removed to provide biphenyl-2-ylcarbamic acid 1-[2-(4-{[(R)-2-(tert-butyldimethylsilanyloxy)-2-(3-formylamino-4-hydroxyphenyl)ethylimino]methyl}-2,5-dimethylphenylcarbamoyl)ethyl]piperidin-4-yl ester (12 g) as a yellow-orange solid.

Step D—Biphenyl-2-ylcarbamic Acid 1-[2-(4-{[(R)-2-(tert-Butyldimethylsilanyloxy)-2-(3-formylamino-4-hydroxyphenyl)ethylamino]methyl}-2,5-dimethylphenyl-carbamoyl)ethyl]piperidin-4-yl Ester To a hydrogenation flask was added biphenyl-2-ylcarbamic acid 1-[2-(4-{[(R)-2-(tert-butyldimethylsilanyloxy)-2-(3-formylamino-4-hydroxyphenyl)ethylimino]methyl}-2,5-dimethylphenylcarbamoyl)ethyl]piperidin-4-yl ester (4.6 g) and 2-methyltetrahydrofuran (50 mL). The resulting mixture was stirred until the solid dissolved (about 5 min.) and then the mixture was purged with nitrogen. Platinum on carbon (920 mg, 5 wt. %, support activated carbon) was added and the mixture was hydrogenated at 50 psi (Parr shaker) for 6 hours. The mixture was then filtered through Celite and the Celite was washed with 2-methyltetrahyrofuran (10 mL). To the filtrate was added a thiopropyl-modified silica gel (20% of weight of solution, Silicycle) and this mixture was stirred at 25° C. to 30° C. for 3 hours. The mixture was then filtered through Celite and concentrated to remove the solvent. The residue was dissolved in methanol (5 mL per gram of residue) and then the resulting solution was added slowly to a vigorously stirred 1:1 mixture of saturated aqueous sodium bicarbonate and water (40 mL per gram of residue). The resulting off-white slurry was stirred for 20 minutes and then filtered. The filter cake was washed with water (20 volumes), air dried for 3 hours and then dried in vacuum at room temperature overnight to provide biphenyl-2-ylcarbamic acid 1-[2-(4-{[(R)-2-(tert-butyldimethylsilanyloxy)-2-(3-formylamino-4-hydroxyphenyl)ethylamino]methyl}-2,5-dimethylphenyl-carbamoyl)ethyl]piperidin-4-yl ester (80% recovery, about 96% purity).

Step E—Biphenyl-2-ylcarbamic Acid 1-[2-(4-{[(R)-2-(3-Formylamino-4-hydroxyphenyl)-2-hydroxyethylamino]methyl}-2,5-dimethylphenyl-carbamoyl)ethyl]piperidin-4-yl Ester L-Tartrate Salt To a 200 mL round-bottom flask was added biphenyl-2-ylcarbamic acid 1-[2-(4-{[(R)-2-(tert-butyldimethylsilanyloxy)-2-(3-formylamino-4-hydroxyphenyl)ethylamino]-methyl}-2,5-dimethylphenylcarbamoyl)ethyl]piperidin-4-yl ester (3.8 g, 4.8 mmol) and 2-methyltetrahydrofuran (40 mL). The resulting mixture was stirred at room temperature until the ingredients dissolved (about 15 min.) and then triethylamine trihydrofluoride (0.94 mL, 5.76 mmol) was added and the resulting mixture was stirred at 25° C. for about 24 hours. To this mixture was added a 1:1 mixture of saturated aqueous sodium bicarbonate and water (40 mL) and 2-methyltetrahydrofuran and the resulting mixture was stirred until the solid dissolved (solution pH about 8). The layers were separated and the organic layer was washed with brine (30 mL), dried over anhydrous sodium sulfate, filtered and concentrated on a rotary evaporator. The residue was dissolved in 2-methyltetrahydrofuran (50 mL) and solid L-tartaric acid (650 mg) was added. The resulting mixture was stirred at 25° C. to 30° C. for 18 hours and then filtered through filter paper. The filter cake was washed with 2-methyltetrahydrofuran (10 mL), isopropanol (10 mL) and immediately put under vacuum to provide biphenyl-2-ylcarbamic acid 1-[2-(4-{[(R)-2-(3-formylamino-4-hydroxyphenyl)-2-hydroxyethylamino]methyl}-2,5-dimethylphenyl-carbamoyl)ethyl]piperidin-4-yl ester L-tartaric acid salt (3.7 g, >97% purity).

Step F—Biphenyl-2-ylcarbamic Acid 1-[2-(4-{[(R)-2-(3-Formylamino-4-hydroxyphenyl)-2-hydroxyethylamino]methyl}-2,5-dimethylphenylcarbamoyl)-ethyl]piperidin-4-yl Ester To a 250 mL round-bottom flask was added biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester L-tartaric acid salt (3.5 g) and methanol (35 mL) and the resulting mixture was stirred for 15 min. A 1:1 mixture of saturated aqueous sodium bicarbonate and water (70 mL) was added over a 5 min. period and stirring was continued for 2 hours. The resulting off-white slurry was filtered and the filter cake was washed with water (20 mL), air dried for 2 hours and then dried in a vacuum overnight to provide biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)-ethyl]piperidin-4-yl ester (2.3 g) as a semi-crystalline free base.

$^1$H and $^{13}$C NMR spectra were obtained for a sample of biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)-ethyl]piperidin-4-yl ester (22.2 mg in about 0.75 mL of DMSO-$d_6$) at ambient temperature using a JEOL ECX-400 NMR spectrometer: $^1$H NMR (400 MHz, DMSO-$d_6$), major isomer, 69.64 (br, 1H), 9.54 (br s, 1H), 9.43 (s, 1H), 8.67 (s, 1H), 8.26 (s, 1H), 8.03 (d, J=1.9, 1H), 7.25-7.45 (m, 9H), ~7.3 (nd, 1H), 7.07 (s, 1H), 6.88 (dd, J=8.2, 1.9, 1H), 6.79 (d, J=8.2, 1H), 5.15 (br, 1H), 4.53 (dd, J=7.3, 4.7, 1H), 4.47 (m, 1H), ~3.65 and 3.60 (AB pair, 2H), 2.68 (br m, 2H), ~2.59 (nd, 4H), 2.44 (br t, J=6.5, 2H), 2.20 (s, 3H), ~2.17 (br m, 2H), 2.14 (s, 3H), 1.73 (br, 2H), 1.44 (br q, J=9.0, 2H). $^1$H NMR (400 MHz, DMSO-$d_6$), minor isomer, 69.64 (br, 1H), 9.43 (s 1H), 9.26 (br d, J=7.0, 1H), 8.67 (s, 1H), 8.50 (br d, J=7.0, 1H), 7.25-7.45 (m, 9H), 7.3 (nd, 1H), 7.07 (s, 1H), ~7.07 (nd, 1H), 6.95 (dd, J=8.3, 1.8, 1H), 6.83 (d, J=8.3, 1H), 5.15 (br, 1H), 4.47 (m, 1H), 3.65 and ~3.60 (AB pair, 2H), 2.68 (br m, 2H), ~2.59 (nd, 2H), 2.44 (br t, J=6.5, 2H), 2.20 (s, 3H), ~2.17 (br m, 2H), 2.14 (s, 3H), 1.73 (br, 2H), 1.44 (br q, J=~9.0, 2H). $^{13}$C NMR (100 MHz, DMSO-$d_6$), major isomer, δ 170.0, 159.9, 153.9, 145.5, 139.3, 137.6, 135.2, 135.0, 134.8, 133.4, 133.4, 130.2, 130.2, 128.6, 128.2, 127.8, 127.4, 127.2, 127.0, 126.1, 125.7, 125.6, 121.7, 118.6, 114.5, 71.4, 70.0, 57.4, 53.9, 50.3, 50.1, 33.7, 30.7, 18.2, 17.5. $^{13}$C NMR (100 MHz, DMSO-$d_6$), minor isomer, δ 170.0, 163.4, 153.9, 147.8, 139.3, 137,6, 135.7, 135.2, 135.0, 134.8, 133.4, 133.4, 130.2, 130.2, 128.6, 128.2, 127.8, 127.4, 127.2, 127.0, 126.1, 125.7, 123.0, 119.6, 115.6, 71.0, 70.0, 57.3, 53.9, 50.3, 50.1, 33.7, 30.7, 18.2, 17.5. The $^1$H and $^{13}$C NMR spectra showed the presence of a major isomer (about 82 mole percent) and a minor isomer (about 18 mole percent) believed to be rotational isomers resulting from hindered rotation about the —NH—C(O)H bond. The phenyl group is believed to be syn to the carbonyl oxygen in the major isomer and anti in the minor isomer.

Example 7

Seed Crystals of Form II of Biphenyl-2-ylcarbamic Acid 1-[2-(4-{[(R)-2-(3-Formylamino-4-hydroxyphenyl)-2-hydroxyethylamino]methyl}-2,5-dimethylphenylcarbamoyl)ethyl]piperidin-4-yl Ester Semi-crystalline biphenyl-2-ylcarbamic acid 1-[2-(4-{[(R)-2-(3-formylamino-4-hydroxyphenyl)-2-hydroxyethylamino]methyl}-2,5-dimethylphenyl-carbamoyl)ethyl]piperidin-4-yl ester (500 mg) was dissolved in methanol (50 mL) and water was added until the cloud point was reached. The resulting mixture was stirred at 25° C. for 3 hours and the resulting crystalline material was isolated by filtration to provide crystalline biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester (420 mg). This crystalline free base was determined to have a differential scanning calorimetry (DSC) trace that exhibit a peak in endothermic heat flow at about 142° C. to about 150° C.; and a powder x-ray diffraction (PXRD) pattern having significant diffraction peaks, among other peaks, at 2θ values of about 20.7±0.3, 21.6±0.3, 22.5±0.3 and 23.2±0.3. This crystalline free base form is designated as Form II. Additional information on Form II and other crystalline free base forms of this compound is disclosed in commonly-assigned U.S. application Ser. No. 11/789,154, filed on even date herewith and U.S. Provisional Application No. 60/794,709, filed Apr. 25, 2006; the disclosures of which are incorporated herein by reference in their entirety.

Example 8

Crystallization of Form II of Biphenyl-2-ylcarbamic acid 1-[2-(4-{[(R)-2-(3-Formylamino-4-hydroxyphenyl)-2-hydroxyethylamino]methyl}-2,5-dimethylphenylcarbamoyl)ethyl]piperidin-4-yl Ester To a 3 L three-necked round-bottomed flask equipped with an over-head stirrer, temperature control and addition funnel was added semi-crystalline biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester (14 g) and methanol (1.4 L). Water (500 mL) was added in one portion and then additional water (200 mL) was added slowly until the cloud point was reached. Seed crystals of biphenyl-2-ylcarbamic acid 1-[2-(4-{[(R)-2-(3-formylamino-4-hydroxyphenyl)-2-hydroxyethylamino]methyl}-2,5-dimethylphenyl-carbamoyl)ethyl]piperidin-4-yl ester Form II (50 mg) were added and the resulting mixture was stirred at 25° C. for 3 hours at which time a free-flowing slurry had developed. Water (300 mL) was added over a 15-minute period and the resulting mixture was stirred at 25° C. overnight. The mixture was then filtered and the filter cake was washed with water (100 mL), air dried for about 2 hours and then dried under vacuum at room temperature for 48 hours to provide crystalline biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl] piperidin-4-yl ester (12.5 g, 99.6% purity). This crystalline salt was determined to be Form II.

Example 9

Biphenyl-2-ylcarbamic Acid 1-[2-(4-Formyl-2,5-dimethylphenylcarbamoyl)ethyl]-piperidin-4-yl Ester Step A—4-Iodo-2,5-dimethylphenylamine To a solution of 2,5-dimethylaniline (20 g, 165 mmol) in a 1:1 mixture of dichloromethane and methanol (400 mL) was added sodium bicarbonate (20.8 g, 250 mmol) and tetramethylammonium dichloroiodate(I) (44.7 g, 165 mmol). The resulting mixture was stirred at room temperature for 1 hour and then water was added (500 mL). The organic layer was removed and washed with 5% aqueous sodium thiosulfate (500 mL) and brine (500 mL). The organic layer was then dried over anhydrous magnesium sulfate, filtered and concentrated under vacuum to provide 4-iodo-2,5-dimethylphenylamine (39.6 g, 98% yield). The product was used without further purification.

Step B—N-(4-Iodo-2,5-dimethylphenyl)acrylamide

To a solution of 4-iodo-2,5-dimethylphenylamine (37.2 g, 151 mmol) in dichloromethane (500 mL) was added sodium bicarbonate (25.4 g, 302 mmol). The resulting mixture was cooled to 0° C. and acryolyl chloride (12.3 mL, 151 mmol) was added slowly over a period of 25 minutes. The resulting mixture was stirred at room temperature overnight and then filtered. The volume of the filtrate was reduced to about 100 mL and a precipitate formed. The precipitate was filtered, dried, washed with water (1 L) and then dried again to afford N-(4-iodo-2,5-dimethylphenyl)acrylamide (42.98 g, 95% purity, 90% yield). The product was used without further purification.

Step C—Biphenyl-2-ylcarbamic Acid 1-[2-(4-Iodo-2,5-dimethylphenylcarbamoyl)-ethyl]piperidin-4-yl Ester To a solution of N-(4-iodo-2,5-dimethylphenyl)acrylamide (32.2 g, 107 mmol) in a 6:1 v/v mixture of N,N-dimethylformamide and isopropanol (700 mL) was added biphenyl-2-ylcarbamic acid piperidin-4-yl ester (36.3 g, 123 mmol). The resulting mixture was heated at 50° C. for 24 hours and then at 80° C. for 24 hours. The reaction mixture was then cooled to room temperature and concentrated under vacuum. The residue was dissolved in dichloromethane (1 L) and this solution was washed with 1N aqueous hydrochloric acid (500 mL), water (500 mL), brine (500 mL) and saturated aqueous sodium bicarbonate solution (500 mL). The organic layer was then dried over anhydrous magnesium sulfate and filtered. Ethanol (400 mL) was added and the resulting mixture was concentrated under vacuum to a volume of about 400 mL, at which time a precipitate had formed. The precipitate was filtered and dried to afford biphenyl-2-ylcarbamic acid 1-[2-(4-iodo-2,5-dimethylphenylcarbamoyl)ethyl]piperidin-4-yl ester (59.6 g, 84% purity, 79% yield). m/z: [M+H]$^+$ calcd for $C_{29}H_{32}IN_3O_3$ 598.49; found 598.5.

Step D—4-{3-[4-(Biphenyl-2-ylcarbamoyloxy)piperidin-1-yl]propionylamino}-2,5-dimethylbenzoic Acid Methyl Ester To a solution of biphenyl-2-ylcarbamic acid 1-[2-(4-iodo-2,5-dimethylphenylcarbamoyl)ethyl]piperidin-4-yl ester (56 g, 94 mmol) in a 5:1 v/v mixture of N,N-dimethylformamide and methanol (600 mL) were added diisopropylethylamine (49 mL, 281 mmol), 1,3-bis(diphenylphosphino)propane (3.9 g, 9.4 mmol) and palladium(II) acetate (2.1 g, 9.4 mmol). The resulting mixture was purged with carbon monoxide and then stirred overnight at 70° C. to 80° C. under a carbon monoxide atmosphere (balloon pressure). The reaction mixture was concentrated under vacuum and the residue was dissolved in dichloromethane (500 mL). This mixture was washed with 1N aqueous hydrochloric acid (500 mL), water (500 mL) and then brine (500 mL). The organic layer was then dried over anhydrous magnesium sulfate, filtered and then concentrated under vacuum. The residue was mixed with ethanol (about 5:1 v/w ethanol to residue) and the mixture was heated until all solid material dissolved. This solution was allowed to slowly cool to room temperature and the resulting precipitate was isolated by filtration to afford 4-{3-[4-(biphenyl-2-ylcarbamoyloxy)piperidin-1-yl]propionylamino}-2,5-dimethylbenzoic acid methyl ester (47.3 g, 97% purity, 92% yield). m/z: [M+H]$^+$ calcd for $C_{31}H_{35}N_3O_5$ 530.63; found 530.4.

Step E—Biphenyl-2-ylcarbamic Acid 1-[2-(4-Hydroxymethyl-2,5-dimethyl-phenylcarbamoyl)ethyl]piperidin-4-yl Ester To a solution of 4-{3-[4-(biphenyl-2-ylcarbamoyloxy)piperidin-1-yl]propionylamino}-2,5-dimethylbenzoic acid methyl ester (49.8 g, 93.9 mmol) in tetrahydrofuran (200 mL) was cooled to 0° C. and lithium aluminum hydride (10.7 g, 281.7 mmol) added portion-wise (10×1.07 g). The resulting mixture was stirred for 3 hours and then water (10.7 mL) was added, followed by 1N aqueous sodium hydroxide (10.7 mL) and additional water (32.1 mL). This mixture was stirred overnight and then filtered. The organic layer was concentrated under vacuum and the residue was mixed with ethyl acetate (about 5:1 v/w ethyl acetate to residue). This mixture was heated until all the solid material dissolved and then the solution was allowed to cool to room temperature. The resulting precipitate was filtered and dried to afford biphenyl-2-ylcarbamic acid 1-[2-(4-hydroxymethyl-2,5-dimethylphenylcarbamoyl)ethyl]piperidin-4-yl ester (24.6 g, 95% purity, 47.5% yield). This material was used without further purification. m/z: [M+H]$^+$ calcd for $C_{30}H_{35}N_3O_4$ 502.62; found 502.5.

Step F—Biphenyl-2-ylcarbamic Acid 1-[2-(4-Formyl-2,5-dimethylphenylcarbamoyl)ethyl]piperidin-4-yl Ester To a solution of biphenyl-2-ylcarbamic acid 1-[2-(4-hydroxymethyl-2,5-dimethylphenylcarbamoyl)ethyl]piperidin-4-yl ester (5.0 g, 10 mmol) in dichloromethane (200 mL) was added diisopropylethylamine (8.7 mL, 50 mmol) and dimethylsulfoxide (5.6 mL, 100 mmol). The resulting mixture was cooled to 0° C. and sulfur trioxide pyridine complex (8.0 g, 50 mmol) was added. The reaction mixture was stirred for 1 hour at 0° C. and water (300 mL) was added. The organic layer was removed and washed with 1N aqueous hydrochloric acid (300 mL) and brine (300 mL). The organic layer was then dried over anhydrous magnesium sulfate and filtered. The resulting solution containing biphenyl-2-ylcarbamic acid 1-[2-(4-formyl-2,5-dimethylphenylcarbamoyl)ethyl]piperidin-4-yl ester was used without further purification. m/z: [M+H$^+$] calcd for $C_{30}H_{33}N_3O_4$ 500.60; found 500.4.

Example 10

Cell Culture and Membrane Preparation From Cells Expressing Human $M_1$, $M_2$, $M_3$ and $M_4$ Muscarinic Receptors CHO cell lines stably expressing cloned human $hM_1$, $hM_2$, $hM_3$ and $hM_4$ muscarinic receptor subtypes, respectively, were grown to near confluency in Hams F-12 media supplemented with 10% FBS and 250 μg/mL Geneticin. The cells were grown in a 5% $CO_2$, 37° C. incubator and lifted with 2 mM EDTA in dPBS. Cells were collected by 5 minute centrifugation at 650×g, and cell pellets were either stored frozen at −80 EC or membranes were prepared immediately for use. For membrane preparation, cell pellets were resuspended in lysis buffer and homogenized with a Polytron PT-2100 tissue disrupter (Kinematica AG; 20 seconds×2 bursts). Crude membranes were centrifuged at 40,000×g for 15 minutes at 4° C. The membrane pellet was then resuspended with re-suspension buffer and homogenized again with the Polytron tissue disrupter. The protein concentration of the membrane suspension was determined by the method described in Lowry et al., 1951, *Journal of Biochemistry*, 193, 265. All membranes were stored frozen in aliquots at −80° C. or used immediately. Aliquots of prepared $hM_5$ receptor membranes were purchased directly from PerkinElmer, Inc. (Wellesley, Mass.) and stored at −80° C. until use.

Example 11

Radioligand Binding Assay for Muscarinic Receptors

Radioligand binding assays for cloned muscarinic receptors were performed in 96-well microtiter plates in a total assay volume of 100 μL. CHO cell membranes stably expressing either the $hM_1$, $hM_2$, $hM_3$, $hM_4$ or $hM_5$ muscarinic subtype were diluted in assay buffer to the following specific target protein concentrations (μg/well): 10 μg for $hM_1$, 10-15 μg for $hM_2$, 10-20 μg for $hM_3$, 10-20 μg for $hM_4$, and 10-12 μg for $hM_5$ to get similar signals (cpm). The membranes were briefly homogenized using a Polytron tissue disruptor (10 seconds) prior to assay plate addition. Saturation binding studies for determining $K_D$ values of the radioligand were performed using L-[N-methyl-$^3$H]scopolamine methyl chloride ([$^3$H]-NMS) (TRK666, 84.0 Ci/mmol, Amersham Pharmacia Biotech, Buckinghamshire, England) at concentrations ranging from 0.001 nM to 20 nM. Displacement assays for determination of $K_i$ values of test compounds were performed with [$^3$H]-NMS at 1 nM and eleven different test compound concentrations. The test compounds were initially dissolved to a concentration of 400 μM in dilution buffer and then serially diluted 5× with dilution buffer to final concentrations ranging from 10 pM to 100 μM. The addition order and volumes to the assay plates were as follows: 25 μL radioligand, 25 μL diluted test compound, and 50 μL membranes. Assay plates were incubated for 60 minutes at 37° C. Binding reactions were terminated by rapid filtration over GF/B glass fiber filter plates (PerkinElmer, Inc.) pre-treated in 1% BSA. Filter plates were rinsed three times with wash buffer (10 mM HEPES) to remove unbound radioactivity. The plates were then air-dried and 50 μL Microscint-20 liquid scintillation fluid (PerkinElmer, Inc.) were added to each well. The plates were then counted in a PerkinElmer Topcount liquid scintillation counter (PerkinElmer, Inc.). Binding data were analyzed by nonlinear regression analysis with the GraphPad Prism Software package (GraphPad Software, Inc., San Diego, Calif.) using the one-site competition model. $K_i$ values for test compounds were calculated from observed $IC_{50}$ values and the $K_D$ value of the radioligand using the Cheng-Prusoff equation (Cheng Y; Prusoff W H. (1973) *Biochemical Pharmacology*, 22(23):3099-108). $K_i$ values were converted to $pK_i$ values to determine the geometric mean and 95% confidence intervals. These summary statistics were then converted back to $K_i$ values for data reporting.

In this assay, a lower $K_i$ value indicates that the test compound has a higher binding affinity for the receptor tested. Biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester (compound IIa) was found to have a $K_i$ value of less than 10 nM for the $M_1$, $M_2$, $M_3$, $M_4$ and $M_5$ muscarinic receptor subtypes.

Example 12

Cell Culture and Membrane Preparation From Cells Expressing Human $\beta_1$, $\beta_2$ or $\beta_3$ Adrenergic Receptors Human embryonic kidney (HEK-293) cell lines stably expressing cloned human $\beta_1$ and $\beta_2$ adrenergic receptors or Chinese hamster ovarian (CHO) cell lines stably expressing cloned human $\beta_3$ adrenergic receptors were grown to near confluency in DMEM or Hams F-12 media with 10% FBS in the presence of 500 μg/mL Geneticin. The cell monolayer was lifted with 2 mM EDTA in PBS. Cells were pelleted by centrifugation at 1,000 rpm, and cell pellets were either stored frozen at −80° C. or membranes were prepared immediately for use. For preparation of $\beta_1$ and $\beta_2$ receptor expressing membranes, cell pellets were re-suspended in lysis buffer (10 mM HEPES/HCl, 10 mM EDTA, pH 7.4 at 4° C.) and homogenized using a tight-fitting Dounce glass homogenizer (30 strokes) on ice. For the more protease-sensitive $\beta_3$ receptor expressing membranes, cell pellets were homogenated in lysis buffer (10 mM Tris/HCl, pH 7.4) supplemented with one tablet of "Complete Protease Inhibitor Cocktail Tablets with 2 mM EDTA" per 50 mL buffer (Roche Molecular Biochemicals, Indianapolis, Ind.). The homogenate was centrifuged at 20,000×g, and the resulting pellet was washed once with lysis buffer by re-suspension and centrifugation as above. The final pellet was then re-suspended in ice-cold binding assay buffer (75 mM Tris/HCl pH 7.4, 12.5 mM $MgCl_2$, 1 mM EDTA). The protein concentration of the membrane suspension was determined by the methods described in Lowry et al., 1951, *Journal of Biological Chemistry*, 193, 265; and Bradford, *Analytical Biochemistry*, 1976, 72, 248-54. All membranes were stored frozen in aliquots at −80° C. or used immediately.

Example 13

Radioligand Binding Assay for Human $\beta_1$, $\beta_2$ and $\beta_3$ Adrenergic Receptors Binding assays were performed in 96-well microtiter plates in a total assay volume of 100 μL with 10-15 μg of membrane protein containing the human $\beta_1$, $\beta_2$ or $\beta_3$ adrenergic receptors in assay buffer (75 mM Tris/HCl pH 7.4 at 25° C., 12.5 mM MgCl$_2$, 1 mM EDTA, 0.2% BSA). Saturation binding studies for determining K$_d$ values of the radioligand were done using [$^3$H]-dihydroalprenolol (NET-720, 100 Ci/mmol, PerkinElmer Life Sciences Inc., Boston, Mass.) for the $\beta_1$ and $\beta_2$ receptors and [$^{125}$I]-(−)-iodocyanopindolol (NEX-189, 220 Ci/mmol, PerkinElmer Life Sciences Inc., Boston, Mass.) at 10 or 11 different concentrations ranging from 0.01 nM to 20 nM. Displacement assays for determination of K$_i$ values of test compounds were done with [$^3$H]-dihydroalprenolol at 1 nM and [$^{125}$I]-(−)-iodocyanopindolol at 0.5 nM for 10 or 11 different concentrations of test compound ranging from 10 pM to 10 µM. Non-specific binding was determined in the presence of 10 µM propranolol. Assays were incubated for 1 hour at 37° C., and then binding reactions were terminated by rapid filtration over GF/B for the $\beta_1$ and $\beta_2$ receptors or GF/C glass fiber filter plates for the $\beta_3$ receptors (Packard BioScience Co., Meriden, Conn.) pre-soaked in 0.3% polyethyleneimine. Filter plates were washed three times with filtration buffer (75 mM Tris/HCl pH 7.4 at 4° C., 12.5 mM MgCl$_2$, 1 mM EDTA) to remove unbound radioactivity. The plates were then dried and 50 µL of Microscint-20 liquid scintillation fluid (Packard BioScience Co., Meriden, Conn.) was added and plates were counted in a Packard Topcount liquid scintillation counter (Packard BioScience Co., Meriden, Conn.). Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 µM propranolol. K$_i$ values for test compounds were calculated from observed IC$_{50}$ values and the K$_d$ value of the radioligand using the Cheng-Prusoff equation (Cheng Y, and Prusoff W H., *Biochemical Pharmacology*, 1973, 22, 23, 3099-108).

In this assay, a lower K$_i$ value indicates that a test compound has a higher binding affinity for the receptor tested. Biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester (compound IIa) was found to have a K$_i$ value of less than 10 nM for the $\beta_2$ adrenergic receptor and K$_i$ values greater than 1000 nM for the $\beta_1$ and $\beta_3$ adrenergic receptors.

Example 14

Functional Assays of Antagonism for Muscarinic Receptor Subtypes

Assay A—Blockade of Agonist-Mediated Inhibition of cAMP Accumulation

In this assay, the functional potency of a test compound as an antagonist for the hM$_2$ receptor was determined by measuring the ability of the test compound to block oxotremorine-inhibition of forskolin-mediated cAMP accumulation in CHO-K1 cells expressing the hM$_2$ receptor. cAMP assays were performed in a radioimmunoassay format using the Flashplate Adenylyl Cyclase Activation Assay System with $^{125}$I-cAMP (NEN SMP004B, PerkinElmer Life Sciences Inc., Boston, Mass.), according to the manufacturer's instructions. Cells were rinsed once with dPBS and lifted with Trypsin-EDTA solution (0.05% trypsin/0.53 mM EDTA) as described in the Cell Culture and Membrane Preparation section above. The detached cells were washed twice by centrifugation at 650×g for five minutes in 50 mL dPBS. The cell pellet was then re-suspended in 10 mL dPBS, and the cells were counted with a Coulter Z1 Dual Particle Counter (Beckman Coulter, Fullerton, Calif.). The cells were centrifuged again at 650×g for five minutes and re-suspended in stimulation buffer to an assay concentration of 1.6×10$^6$ to 2.8×10$^6$ cells/mL.

The test compound was initially dissolved to a concentration of 400 µM in dilution buffer (dPBS supplemented with 1 mg/mL BSA (0.1%)), and then serially diluted with dilution buffer to final molar concentrations ranging from 100 µM to 0.11 nM. Oxotremorine was diluted in a similar manner.

To measure oxotremorine inhibition of adenylyl cyclase activity, 25 µL forskolin (25 µM final concentration diluted in dPBS), 25 µL diluted oxotremorine, and 50 µL cells were added to agonist assay wells. To measure the ability of a test compound to block oxotremorine-inhibited adenylyl cyclase activity, 25 µL forskolin and oxotremorine (25 µM and 5 µM final concentrations, respectively, diluted in dPBS), 25 µL diluted test compound, and 50 µL cells were added to remaining assay wells.

Reactions were incubated for 10 minutes at 37° C. and stopped by addition of 100 µL ice-cold detection buffer. Plates were sealed, incubated overnight at room temperature and counted the next morning on a PerkinElmer TopCount liquid scintillation counter (PerkinElmer Inc., Wellesley, Mass.). The amount of cAMP produced (pmol/well) was calculated based on the counts observed for the samples and cAMP standards, as described in the manufacturer's user manual. Data was analyzed by nonlinear regression analysis with the GraphPad Prism Software package (GraphPad Software, Inc., San Diego, Calif.) using the non-linear regression, one-site competition equation. The Cheng-Prusoff equation was used to calculate the K$_{obs}$, using the EC$_{50}$ of the oxotremorine concentration-response curve and the oxotremorine assay concentration as the K$_D$ and [L], respectively.

In this assay, a lower K$_{obs}$ value indicates that the test compound has a higher functional activity at the receptor tested. Biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester (compound IIa) was found to have a K$_{obs}$ value of less than about 10 nM for blockade of oxotremorine-inhibition of forskolin-mediated cAMP accumulation in CHO-K1 cells expressing the hM$_2$ receptor.

Assay B—Blockade of Agonist-Mediated [$^{35}$S]GTPγS Binding

In this functional assay, the functional potency of a test compound as an antagonist of the hM$_2$ receptor was determined by measuring the ability of the test compound to block oxotremorine-stimulated [$^{35}$S]GTPγS binding in CHO-K1 cells expressing the hM$_2$ receptor.

At the time of use, frozen membranes were thawed and then diluted in assay buffer with a final target tissue concentration of 5 to 10 µg protein per well. The membranes were briefly homogenized using a Polytron PT-2100 tissue disrupter and then added to the assay plates.

The EC$_{90}$ value (effective concentration for 90% maximal response) for stimulation of [$^{35}$S]GTPγS binding by the agonist oxotremorine was determined in each experiment.

To determine the ability of a test compound to inhibit oxotremorine-stimulated [$^{35}$S]GTPγS binding, the following was added to each well of 96 well plates: 25 µL of assay buffer with [$^{35}$S]GTPγS (0.4 nM), 25 µL of oxotremorine(EC$_{90}$) and GDP (3 uM), 25 µL of diluted test compound and 25 µL CHO cell membranes expressing the hM$_2$ receptor. The assay plates were then incubated at 37° C. for 60 minutes. The assay plates were filtered over 1% BSA-pretreated GF/B filters using a PerkinElmer 96-well harvester. The plates were rinsed with ice-cold wash buffer for 3×3 seconds and then air or vacuum dried. Microscint-20 scintillation liquid (50 μL) was added to each well, and each plate was sealed and radioactivity counted on a Topcounter (PerkinElmer). Data were analyzed by nonlinear regression analysis with the GraphPad Prism Software package (GraphPad Software, Inc., San Diego, Calif.) using the non-linear regression, one-site competition equation. The Cheng-Prusoff equation was used to calculate the $K_{obs}$, using the $IC_{50}$ values of the concentration-response curve for the test compound and the oxotremorine concentration in the assay as the $K_D$ and [L], ligand concentration, respectively.

In this assay, a lower $K_{obs}$ value indicates that the test compound has a higher functional activity at the receptor tested. Biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester (compound IIa) was found to have a $K_{obs}$ value of less than about 10 nM for blockade of oxotremorine-stimulated [$^{35}$S]GTPγS binding in CHO-K1 cells expressing the $hM_2$ receptor.

Assay C—Blockade of Agonist-Mediated Calcium Release via FLIPR Assays

In this functional assay, the functional potency of a test compound as an antagonist of $hM_1$, $hM_3$ and $cM_5$ receptors was determined by measuring the ability of the test compound to inhibit agonist-mediated increases in intracellular calcium.

CHO cells stably expressing the receptors were seeded into 96-well FLIPR plates the night before the assay was done. Seeded cells were washed twice with FLIPR buffer (10 mM HEPES, pH 7.4, 2 mM calcium chloride, 2.5 mM probenecid in Hank's Buffered Salt Solution (HBSS) without calcium and magnesium) using Cellwash (MTX Labsystems, Inc.) to remove growth media. After washing, each well contained 50 μL of FLIPR buffer. The cells were then incubated with 50 μL/well of 4 μM FLUO-4 μM (a 2× solution was made) for 40 minutes at 37° C., 5% carbon dioxide. Following the dye incubation period, cells were washed two times with FLIPR buffer, leaving a final volume of 50 μL in each well.

The dose-dependent stimulation of intracellular $Ca^{2+}$ release for oxotremorine was determined so that the test compound could be measured against oxotremorine stimulation at an $EC_{90}$ concentration. Cells were first incubated with compound dilution buffer for 20 minutes and then oxotremorine was added. An $EC_{90}$ value for oxotremorine was generated according to the method detailed in the FLIPR measurement and data reduction section below, in conjunction with the formula $EC_F = ((F/100-F)^{1/H}) * EC_{50}$. An oxotremorine concentration of $3 \times EC_F$ was prepared in stimulation plates such that an $EC_{90}$ concentration of oxotremorine was added to each well in test assay plates.

The parameters used for the FLIPR were: exposure length of 0.4 seconds, laser strength of 0.5 watts, excitation wavelength of 488 nm, and emission wavelength of 550 nm. Baseline was determined by measuring the change in fluorescence for 10 seconds prior to addition of oxotremorine. Following oxotremorine stimulation, the FLIPR continuously measured the change of fluorescence every 0.5 to 1 second for 1.5 minutes to capture the maximum fluorescence change.

The change of fluorescence was expressed as maximum fluorescence minus baseline fluorescence for each well. The raw data was analyzed against the logarithm of test compound concentration by nonlinear regression with GraphPad Prism (GraphPad Software, Inc., San Diego, Calif.) using the built-in model for sigmoidal dose-response. Antagonist $K_{obs}$ values were determined by Prism using the oxotremorine $EC_{50}$ value as the $K_D$ and the oxotremorine $EC_{90}$ for the ligand concentration according to the Cheng-Prusoff equation (Cheng & Prusoff, 1973).

In this assay, a lower $K_{obs}$ value indicates that the test compound has a higher functional activity at the receptor tested. Biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl]piperidin-4-yl ester (compound IIa) was found to have a $K_{obs}$ value of less than about 10 nM for blockade of agonist-mediated calcium release in CHO cells stably expressing the $hM_1$, $hM_3$ and $cM_5$ receptors.

Example 15

Whole-cell cAMP Flashplate Assay in HEK-293 and CHO Cell Lines Heterologously Expressing Human $\beta_1$, $\beta_2$ or $\beta_3$ Adrenergic Receptors cAMP assays were performed in a radioimmunoassay format using the Flashplate Adenylyl Cyclase Activation Assay System with [$^{125}$I]-cAMP (NEN SMP004, PerkinElmer Life Sciences Inc., Boston, Mass.), according to the manufacturers instructions. For the determination of $\beta_1$ and $\beta_2$ receptor agonist potency ($EC_{50}$), HEK-293 cell lines stably expressing cloned human $\beta_1$ and $\beta_2$ receptors were grown to near confluency in DMEM supplemented with 10% FBS and Geneticin (500 μg/mL). For the determination $\beta_3$ receptor agonist potency ($EC_{50}$), CHO-K1 cell line stably expressing cloned human or $\beta_3$ adrenergic receptors was grown to near confluency in Hams F-12 media supplemented with 10% FBS and Geneticin (250 μg/mL). Cells were rinsed with PBS and detached in dPBS (Dulbecco's Phosphate Buffered Saline, without $CaCl_2$ and $MgCl_2$) containing 2 mM EDTA or Trypsin-EDTA solution (0.05% trypsin/0.53 mM EDTA). After counting cells in Coulter cell counter, cells were pelleted by centrifugation at 1,000 rpm and re-suspended in stimulation buffer containing IBMX (PerkinElmer Kit) pre-warmed to room temperature to a concentration of $1.6 \times 10^6$ to $2.8 \times 10^6$ cells/mL. About 40,000 to 80,000 cells per well were used in this assay. Test compounds (10 mM in DMSO) were diluted into PBS containing 0.1% BSA in Beckman Biomek-2000 and tested at 11 different concentrations ranging from 100 μM to 1 μM. Reactions were incubated for 10 min at 37° C. and stopped by adding 100 μL of cold detection buffer containing [$^{125}$I]-cAMP (NEN SMP004, PerkinElmer Life Sciences, Boston, Mass.). The amount of cAMP produced (pmol/well) was calculated based on the counts observed for the samples and cAMP standards as described in the manufacturer's user manual. Data were analyzed by nonlinear regression analysis with the GraphPad Prism Software package (GraphPad Software, Inc., San Diego, Calif.) with the sigmoidal equation. The Cheng-Prusoff equation (Cheng Y, and Prusoff W H., *Biochemical Pharmacology*, 1973, 22, 23, 3099-108) was used to calculate the $EC_{50}$ values.

In this assay, a lower $EC_{50}$ value indicates that the test compound has a higher functional activity at the receptor tested. Biphenyl-2-ylcarbamic acid 1-[2-(4-{[(R)-2-(3-formylamino-4-hydroxyphenyl)-2-hydroxyethylamino]methyl}-2,5-dimethylphenyl-carbamoyl)ethyl]piperidin-4-yl ester (compound IIa) was found to have an $EC_{50}$ value less than about 10 nM for the $\beta_2$ adrenergic receptor; an $EC_{50}$ value of about 30 nM for the $\beta_1$ adrenergic receptor; and an $EC_{50}$ value greater than 700 nM for the β3 adrenergic receptor.

Example 16

Whole-Cell cAMP Flashplate Assay With a Lung Epithelial Cell Line Endogenously Expressing Human $\beta_2$ Adrenergic Receptor In this assay, the agonist potency and intrinsic activity of a test compound were determined using a cell line expressing endogenous levels of the $\beta_2$ adrenergic receptor. Cells from a human lung epithelial cell line (BEAS-2B) (ATCC CRL-9609, American Type Culture Collection, Manassas, Va.) (January B, et al., *British Journal of Pharmacology*, 1998, 123, 4, 701-11) were grown to 75-90% confluency in complete, serum-free medium (LHC-9 medium containing epinephrine and retinoic acid, Biosource International, Camarillo, Calif.). The day before the assay, the medium was switched to LHC-8 (no epinephrine or retinoic acid, Biosource International, Camarillo, Calif.). cAMP assays were performed in a radioimmunoassay format using the Flashplate Adenylyl Cyclase Activation Assay System with [$^{125}$I]-cAMP (NEN SMP004, PerkinElmer Life Sciences Inc., Boston, Mass.), according to the manufacturers instructions.

On the day of the assay, cells were rinsed with PBS, lifted by scraping with 5 mM EDTA in PBS, and counted. Cells were pelleted by centrifugation at 1,000 rpm and re-suspended in stimulation buffer pre-warmed to 37° C. at a final concentration of 600,000 cells/mL. Cells were used at a final concentration of 100,000 to 120,000 cells/well in this assay. Test compounds were serially diluted into assay buffer (75 mM Tris/HCl pH 7.4 at 25° C., 12.5 mM $MgCl_2$, 1 mM EDTA, 0.2% BSA) in Beckman Biomek-2000. Test compounds were tested in the assay at 11 different concentrations, ranging from 10 μM to 10 pM. Reactions were incubated for 10 min at 37° C. and stopped by addition of 100 μL of ice-cold detection buffer. Plates were sealed, incubated over night at 4° C. and counted the next morning in a Topcount scintillation counter (Packard BioScience Co., Meriden, Conn.). The amount of cAMP produced per mL of reaction was calculated based on the counts observed for samples and cAMP standards, as described in the manufacturer's user manual. Data were analyzed by nonlinear regression analysis with the GraphPad Prism Software package (GraphPad Software, Inc., San Diego, Calif.) using the 4-parameter model for sigmoidal dose-response.

In this assay, a lower $EC_{50}$ value indicates that the test compound has a higher functional activity at the receptor tested. Biphenyl-2-ylcarbamic acid 1-[2-(4-{[(R)-2-(3-formylamino-4-hydroxyphenyl)-2-hydroxyethylamino]methyl}-2,5-dimethylphenyl-carbamoyl)ethyl]piperidin-4-yl ester (compound IIa) was found to have an $EC_{50}$ value of less than 10 nM with intrinsic activity value of greater than 0.3 compared with a full $\beta_2$ agonist isoproterenol (1.0).

Example 17

Einthoven Assay for Determining Bronchoprotective Efficacy and Duration

In this assay, the bronchoprotective efficacy and duration of test compounds were determined using guinea pigs. This assay was derived from the procedures described in Einthoven (1892) *Pfugers Arch.* 51: 367-445; and Mohammed et al. (2000) *Pulm Pharmacol Ther.* 13(6):287-92. In this assay, changes in ventilation pressure serve as a surrogate measure of airway resistance. Following pre-treatment with a test compound, muscarinic antagonist potency was determined using bronchoconstrictor dose-response curves to intravenous methacholine in the presence of propranolol. Similarly, $\beta_2$ agonist bronchoprotective potency was determined using histamine. Combined bronchoprotective potency was determined using methacholine in the absence of propranolol.

The assay was conducted using male Duncan-Hartley guinea pigs (Harlan, Indianapolis, Ind.), weighing between 250 and 400 g. A test compound or vehicle (i.e., sterile water) was dosed by inhalation (1H) over a 10 minute time period in a whole body exposure dosing chamber (R+S Molds, San Carlos, Calif.) using 5 mL of dosing solution. Animals were exposed to an aerosol generated from an LC Star Nebulizer Set (Model 22F51, PARI Respiratory Equipment, Inc. Midlothian, Va.) driven by Bioblend (a mixture of 5% $CO_2$; 21% $O_2$; and 74% $N_2$) at a pressure of 22 psi. Pulmonary function was evaluated at various time points after inhalation dosing.

Seventy-five minutes prior to the start of the assay, the guinea pigs were anesthetized with an intramuscular (IM) injection of a mixture of ketamine (43.7 mg/kg/xylazine (3.5 mg/kg)/acepromazine (1.05 mg/kg). A supplemental dose of this mixture (50% of initial dose) was administered as needed. The jugular vein and carotid artery were isolated and cannulated with saline-filled polyethylene catheters (microrenathane and PE-50, respectively, Beckton Dickinson, Sparks, Md.). The carotid artery was connected to a pressure transducer to allow the measurement of blood pressure and the jugular vein cannula was used for IV injection of either methacholine or histamine. The trachea was then dissected free and cannulated with a 14G needle (#NE-014, Small Parts, Miami Lakes, Fla.). Once the cannulations were complete, the guinea pigs were ventilated using a respirator (Model 683, Harvard Apparatus, Inc., MA) set at a stroke volume of 1 mL/100 g body weight but not exceeding 2.5 mL volume, and at a rate of 100 strokes per minute. Ventilation pressure (VP) was measured in the tracheal cannula using a Biopac transducer connected to a Biopac (TSD 137C) pre-amplifier. Body temperature was maintained at 37° C. using a heating pad. Prior to initiating data collection, pentobarbital (25 mg/kg) was administered intraperitoneally (IP) to suppress spontaneous breathing and obtain a stable baseline. The changes in VP were recorded on a Biopac Windows data collection interface. Baseline values were collected for at least 5 minutes, after which time guinea pigs were challenged IV non-cumulatively with 2-fold incremental doses of the bronchoconstrictor (methacholine or histamine). When methacholine was used as the bronchoconstrictor agent, animals were pre-treated with propranolol (5 mg/kg, IV) to isolate the antimuscarinic effects of the test compound. The propranolol was administered 30 minutes prior to construction of the dose-response curve to methacholine or histamine. Changes in VP were recorded using the Acknowledge Data Collection Software (Santa Barbara, Calif.). After the completion of study, the animals were euthanized.

Change in VP was measured in cm of water. Change in VP (cm $H_2O$)=peak pressure (after bronchoconstrictor challenge)−peak baseline pressure. The dose-response curve to methacholine or histamine was fitted to a four parameter logistic equation using GraphPad Prism, version 3.00 for Windows (GraphPad Software, San Diego, Calif.). The following equation was used:

$$Y = \text{Min} + (\text{Max} - \text{Min})/(1 + 10^{((\log ID50 - X)*Hillslope)})$$

where X is the logarithm of dose, Y is the response. Y starts at Min and approaches asymptotically to Max with a sigmoidal shape.

The percent inhibition of the bronchoconstrictor response to a submaximal dose of methacholine or histamine was calculated at each dose of the test compound using the following equation: % Inhibition of response=100−((peak pressure (after bronchoconstrictor challenge, treated)−peak baseline pressure (treated)*100%/(peak pressure (after bronchoconstrictor challenge, water)−peak baseline pressure (water)×100). Inhibition curves were fitted using the four parameter logistic equation from GraphPad software. $ID_{50}$ (dose required to produce 50% inhibition of the bronchoconstrictor response) and Emax (maximal inhibition) were also estimated wherever appropriate.

The magnitude of bronchoprotection at different timepoints after inhalation of the test compound was used to estimate the pharmacodynamic half-life (PD $T_{1/2}$). PD $T_{1/2}$ was determined using a non-linear regression fit using a one-phase exponential decay equation (GraphPad Prism, Version 4.00): Y=Span*exp(−K*X)+Plateau; Starts at Span+Plateau and decays to Plateau with a rate constant K. The PD $T_{1/2}$=0.69/K. Plateau was constrained to 0.

At 1.5 hours post-dose, biphenyl-2-ylcarbamic acid 1-[2-(4-{[(R)-2-(3-formylamino-4-hydroxyphenyl)-2-hydroxyethylamino]methyl}-2,5-dimethylphenylcarbamoyl)ethyl] piperidin-4-yl ester (IIa) was found to have an ID50 of less than about 50 μg/mL for both methacholine-induced bronchoconstriction and histamine-induced bronchoconstriction.

Additionally, this compound produced significant bronchoprotection for up to about 72 hours when administered as a single sub-maximal dose (100 μg/mL). In this assay, salmeterol (3 μg/mL) (a $β_2$ adrenergic receptor agonist) exhibited significant bronchoprotection for 6 to 14 hours; and tiotropium (10 μg/mL) (a muscarinic receptor antagonist) exhibited significant bronchoprotection for greater than 72 hours.

Example 18

Plethysmograph Guinea Pig Assay for Determining Bronchoprotective Efficacy and Duration In this assay, the bronchoprotective efficacy and duration of test compounds was determined using a guinea pig assay.

Groups of 6 male guinea pigs (Duncan-Hartley (HsdPoc: DH) Harlan, Madison, Wis.) weighing between 250 and 350 g were individually identified by cage cards. Throughout the study, animals were allowed access to food and water ad libitum. Test compounds were administered via inhalation over 10 minutes in a whole-body exposure dosing chamber (R&S Molds, San Carlos, Calif.). The dosing chambers were arranged so that an aerosol was simultaneously delivered to 6 individual chambers from a central manifold. Guinea pigs were exposed to an aerosol of a test compound or vehicle (WFI). The aerosols were generated from aqueous solutions using an LC Star Nebulizer Set (Model 22F51, PARI Respiratory Equipment, Inc. Midlothian, Va.) driven by a mixture of gases ($CO_2$=5%, $O_2$=21% and $N_2$=74%) at a pressure of 22 psi. The gas flow through the nebulizer at this operating pressure was approximately 3 L per minute. The generated aerosols were driven into the chambers by positive pressure. No dilution air was used during the delivery of aerosolized solutions. During the 10 minute nebulization, approximately 1.8 mL of solution was nebulized. This value was measured gravimetrically by comparing pre- and post-nebulization weights of the filled nebulizer.

The bronchoprotective effects of test compounds administered via inhalation were evaluated using whole body plethysmography at 1.5, 24, 48 and 72 hours post-dose. Forty-five minutes prior to the start of the pulmonary evaluation, each guinea pig was anesthetized with an intramuscular injection of ketamine (43.75 mg/kg), xylazine (3.50 mg/kg) and acepromazine (1.05 mg/kg). The surgical site was shaved and cleaned with 70% alcohol and a 2 to 3 cm midline incision of the ventral aspect of the neck was made. The jugular vein was isolated and cannulated with a saline-filled polyethylene catheter (PE-50, Becton Dickinson, Sparks, Md.) to allow for intravenous infusions of acetylcholine or histamine in saline. The trachea was then dissected free and cannulated with a 14G teflon tube (#NE-014, Small Parts, Miami Lakes, Fla.). If required, anesthesia was maintained by additional intramuscular injections of the anesthetic mixture. The depth of anesthesia was monitored and adjusted if the animal responded to pinching of its paw or if the respiration rate was greater than 100 breaths per minute.

Once the cannulations were completed, the animal was placed into a plethysmograph (#PLY3114, Buxco Electronics, Inc., Sharon, Conn.) and an esophageal pressure cannula (PE-160, Becton Dickinson, Sparks, Md.) was inserted to measure pulmonary driving pressure. The teflon tracheal tube was attached to the opening of the plethysmograph to allow the guinea pig to breathe room air from outside the chamber. The chamber was then sealed. A heating lamp was used to maintain body temperature and the guinea pig's lungs were inflated three times with 4 mL of air using a 10 mL calibration syringe (#5520 Series, Hans Rudolph, Kansas City, Mo.) to ensure that the lower airways had not collapsed and that the animal did not suffer from hyperventilation.

The pulmonary evaluation was initiated after determining that baseline values were within the range of 0.3 to 0.9 mL per cm $H_2O$ for compliance and within the range of 0.1 to 0.199 cm $H_2O$ per mL per second for resistance. A Buxco pulmonary measurement computer program was used for the collection and derivation of pulmonary values. Starting the program initiated the experimental protocol and data collection. The changes in volume over time that occurred within the plethysmograph with each breath were measured via a Buxco pressure transducer. By integrating this signal over time, a measurement of flow was calculated for each breath. This signal and the pulmonary driving pressure changes, collected using a Sensym pressure transducer (TRD4100), were connected via a Buxco (MAX 2270) preamplifier to a data collection interface (SFT3400 and SFT3813). All other pulmonary parameters are derived from these two inputs.

Baseline values were collected for 5 minutes, after which time the guinea pigs were challenged with either acetylcholine or histamine. When evaluating the muscarinic antagonist effects of a test compound, propanolol (5 mg/Kg, iv) (Sigma-Aldrich, St. Louis, Mo.) was administered 15 minutes prior to challenge with acetylcholine. Acetylcholine (Sigma-Aldrich, St. Louis, Mo.) (0.1 mg/mL) was infused intravenously for 1 minute from a syringe pump (sp210iw, World Precision Instruments, Inc., Sarasota, Fla.) at the following doses and prescribed times from the start of the experiment: 1.9 μg/minute at 5 minutes, 3.8 μg/minute at 10 minutes, 7.5 μg/minute at 15 minutes, 15.0 μg/minute at 20 minutes, 30 μg/minute at 25 minutes and 60 μg/minute at 30 minutes. Alternatively, bronchoprotective effects of the test compound was assessed in the acetylcholine challenge model without pretreatment with propanolol.

When evaluating the $O_2$ adrenergic receptor agonist effects of the test compound, histamine (25 μg/mL) (Sigma-Aldrich, St. Louis, Mo.) was infused intravenously for 1 minute from a syringe pump at the following doses and prescribed times from the start of the experiment: 0.5 μg/minute at 5 minutes, 0.9 µg/minute at 10 minutes, 1.9 µg/minute at 15 minutes, 3.8 µg/minute at 20 minutes, 7.5 µg/minute at 25 minutes and 15 µg/minute at 30 minutes. If resistance or compliance did not returned to baseline values at 3 minutes following each acetylcholine or histamine dose, the guinea pig's lungs were inflated 3 times with 4 mL of air from a 10 mL calibration syringe. The pulmonary parameters recorded included respiration frequency (breaths per minute), compliance (mL per cm $H_2O$) and pulmonary resistance (cm $H_2O$ per mL per second). Once the pulmonary function measurements were completed at minute 35 of this protocol, the guinea pig was removed from the plethysmograph and euthanized by carbon dioxide asphyxiation.

The data were evaluated in one of two ways:

(a) Pulmonary resistance ($R_L$) (cm $H_2O$ per mL per second) was calculated from the ratio of change in pressure to the change in flow. The $R_L$ response to acetylcholine (60 µg/min, 1H) was computed for the vehicle and the test compound. The mean acetylcholine response in vehicle-treated animals, at each pre-treatment time, was calculated and used to compute percent inhibition of acetylcholine response, at the corresponding pre-treatment time, at each test compound dose. Inhibition dose-response curves for '$R_L$' were fitted with a four parameter logistic equation using GraphPad Prism, version 3.00 for Windows (GraphPad Software, San Diego, Calif.) to estimate bronchoprotective ID50 (dose required to inhibit the acetylcholine (60 µg/min) bronchoconstriction response by 50%). The following equation was used:

$$Y = Min + (Max - Min)/(1 + 10^{(\log ID50 - X)*Hillslope})$$

where X is the logarithm of dose, Y is the response (percent inhibition of acetylcholine-induced increase in $R_L$). Y starts at Min and approaches asymptotically to Max with a sigmoidal shape.

(b) The quantity $PD_2$, which is defined as the amount of acetylcholine or histamine needed to cause a doubling of the baseline pulmonary resistance, was calculated using the pulmonary resistance values derived from the flow and the pressure over a range of acetylcholine or histamine challenges using the following equation (which was derived from an equation used to calculate $PC_{20}$ values described in American Thoracic Society. Guidelines for methacholine and exercise challenge testing—1999. *Am J Respir Crit. Care Med.* 2000; 161: 309-329):

$$PD_2 = \text{antilog}\left[\log C_1 + \frac{(\log C_2 - \log C_1)(2R_0 - R_1)}{R_2 - R_1}\right]$$

where:
$C_1$=concentration of acetylcholine or histamine preceding $C_2$
$C_2$=concentration of acetylcholine or histamine resulting in at least a 2-fold increase in pulmonary resistance ($R_L$)
$R_0$=Baseline $R_L$ value
$R_1$=$R_L$ value after $C_1$
$R_2$=$R_L$ value after $C_2$ Statistical analysis of the data was performed using a two tailed Students t-test. A P-value <0.05 was considered significant.

Compound 50 described in U.S. Patent Publication No. US 2004/0167167A1, published Aug. 24, 2004, was tested in this assay. The chemical structure of compound 50 is as follows:

Comparative Compound 50

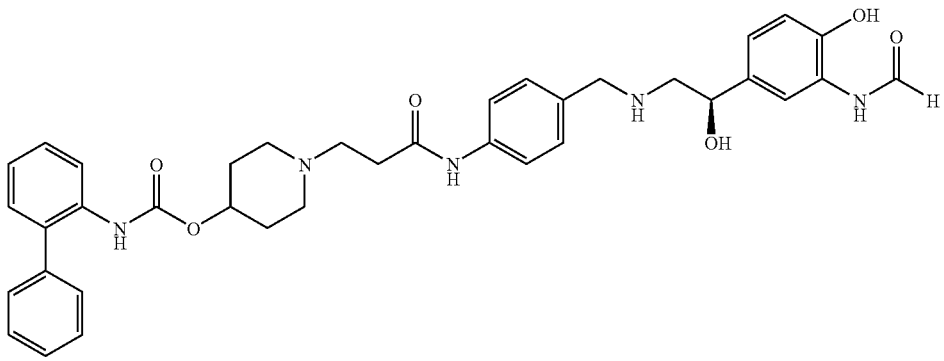

This compound lacks the alkyl groups present on phenyl ring of the compounds of the present invention. In this assay, compound 50 showed no significant bronchoprotection at 24 hours post-dose for doses ranging from 3 µg/mL to 300 µg/mL. The PD2x valves for compound 50 at 24 hours were similar to the vehicle (water) group.

In this assay, salmeterol (100 µg/mL) (a $\beta_2$ adrenergic receptor agonist) exhibited significant bronchoprotection for at least 24 hours; and tiotropium (10 µg/mL) (a muscarinic receptor antagonist) exhibited significant bronchoprotection for at least 24 hours.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A method of producing bronchodilation in a mammal, the method comprising administering to the mammal a bronchodilation-producing amount of a compound of formula I:

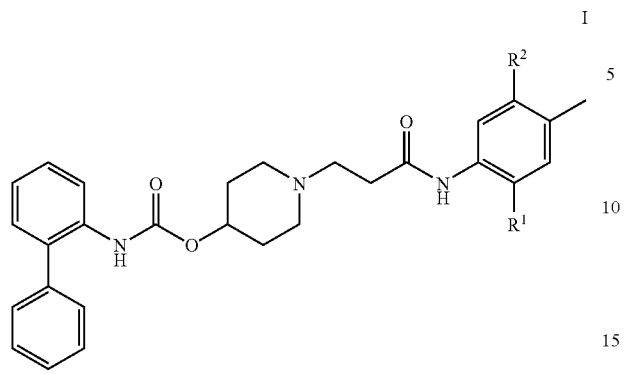

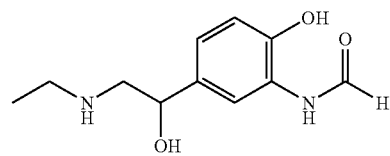

wherein R¹ is methyl or ethyl; R² is methyl or ethyl; or a pharmaceutically acceptable salt or stereoisomer thereof.

2. The method of claim 1, wherein the compound has formula II:

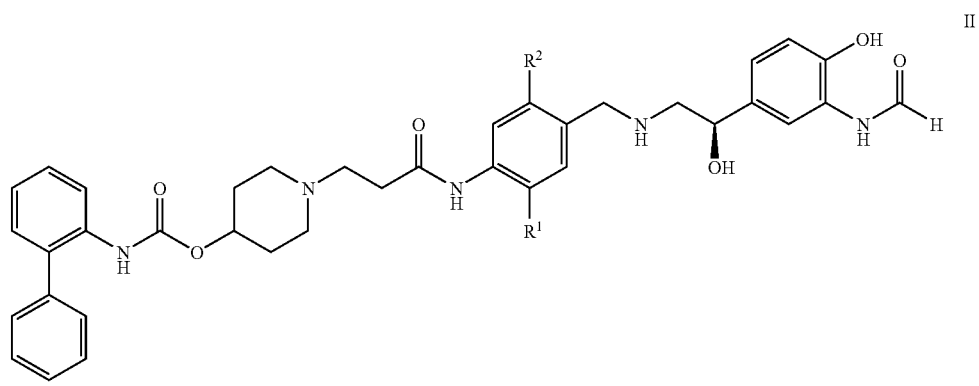

wherein R¹ is methyl or ethyl; R² is methyl or ethyl; or a pharmaceutically acceptable salt thereof.

3. The method of claim 1, wherein the compound has formula IIa:

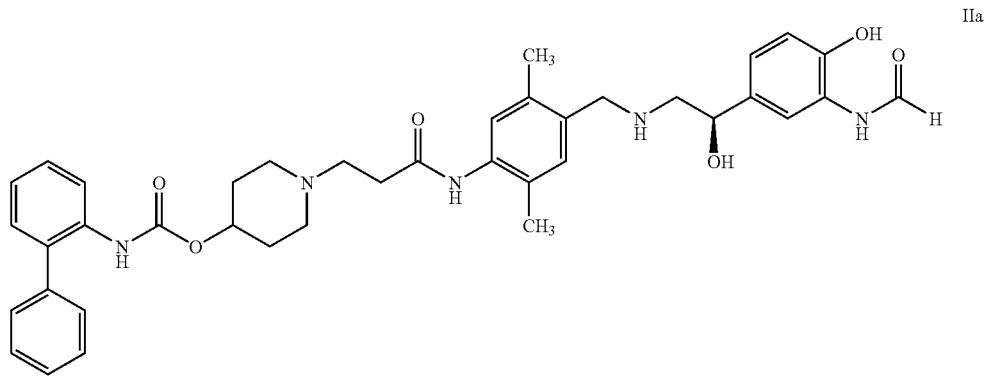

or a pharmaceutically acceptable salt thereof.

4. The method of claim 3, wherein the compound or the salt thereof is administered by inhalation.

5. The method of claim 3, wherein the compound or the salt thereof is in micronized form.

6. A method of treating chronic obstructive pulmonary disease in a patient, the method comprising administering to the patient a compound of formula I:

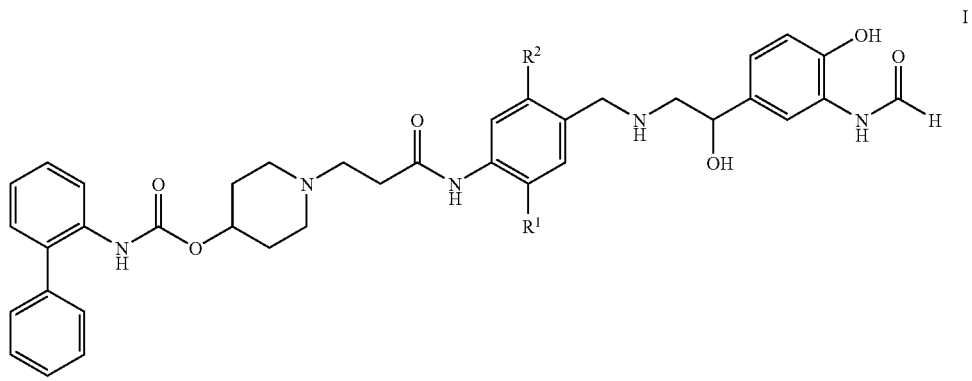

wherein $R^1$ is methyl or ethyl; $R^2$ is methyl or ethyl; or a pharmaceutically acceptable salt or stereoisomer thereof.

7. The method of claim 6, wherein the compound has formula II:

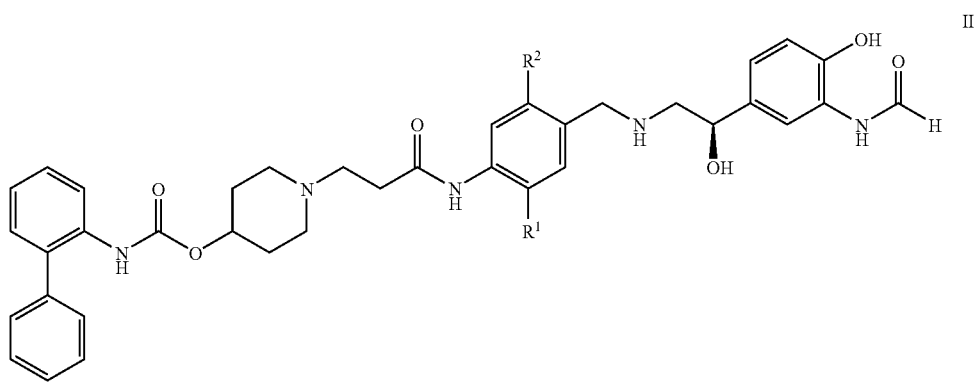

wherein $R^1$ is methyl or ethyl; $R^2$ is methyl or ethyl; or a pharmaceutically acceptable salt thereof.

8. The method of claim 6, wherein the compound has formula IIa:

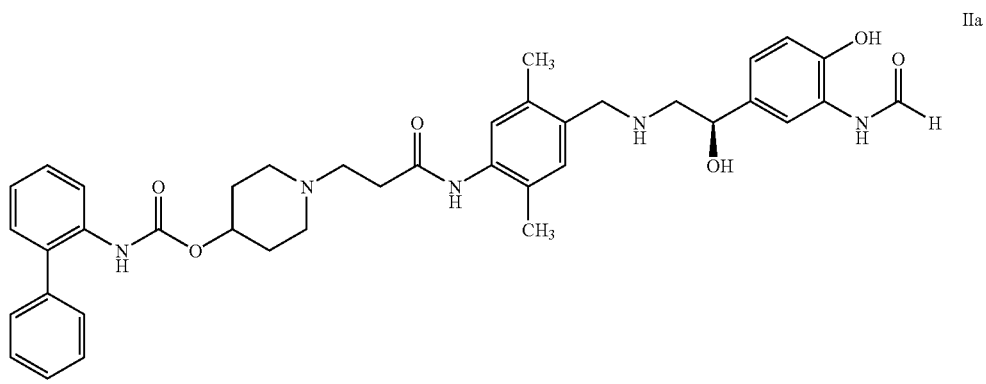

or a pharmaceutically acceptable salt thereof.

9. A method of treating asthma in a patient, the method comprising administering to the patient a compound of formula I:

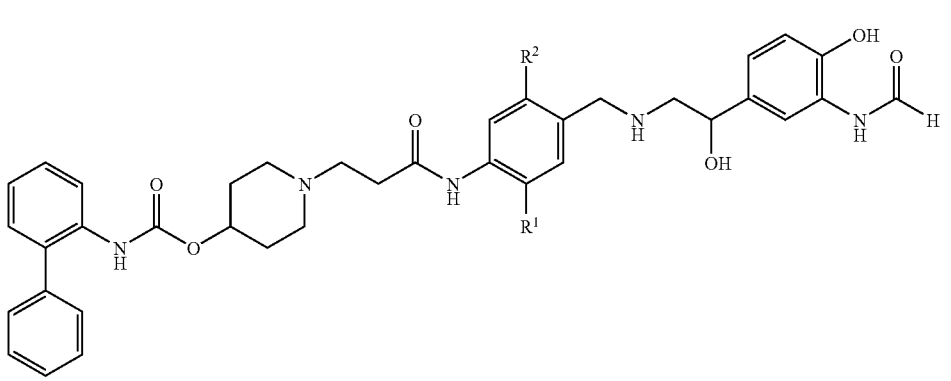

wherein R[1] is methyl or ethyl; R[2] is methyl or ethyl; or a pharmaceutically acceptable salt or stereoisomer thereof.

10. The method of claim 9, wherein the compound has formula II:

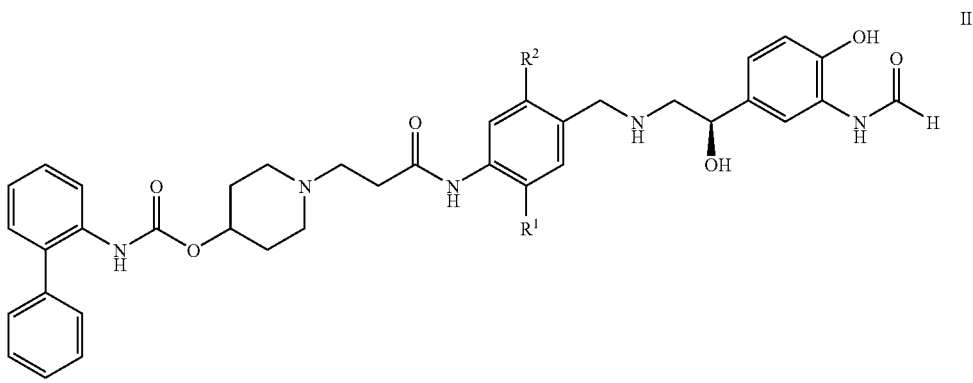

wherein R[1] is methyl or ethyl; R[2] is methyl or ethyl; or a pharmaceutically acceptable salt thereof.

11. The method of claim 9, wherein the compound has formula IIa:

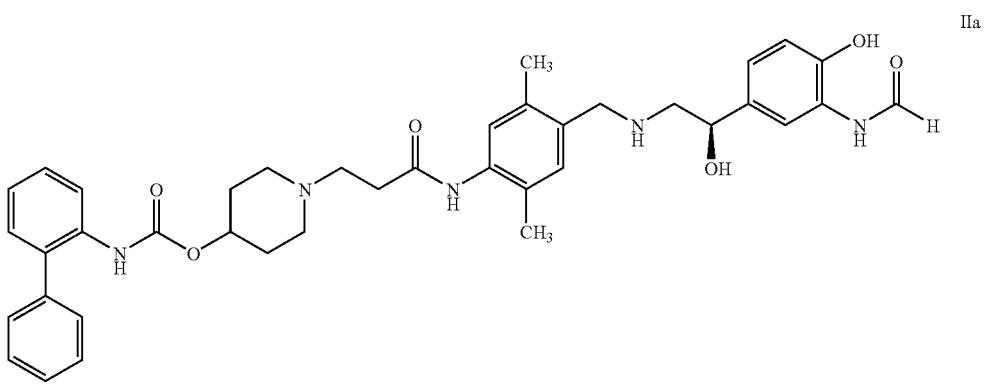

or a pharmaceutically acceptable salt thereof.

* * * * *